United States Patent
Cannata et al.

(10) Patent No.: US 11,980,778 B2
(45) Date of Patent: *May 14, 2024

(54) HISTOTRIPSY SYSTEMS AND METHODS

(71) Applicant: HistoSonics, Inc., Plymouth, MN (US)

(72) Inventors: Jonathan M. Cannata, Ann Arbor, MI (US); Ryan M. Miller, Saline, MI (US); Alexander P. Duryea, Ann Arbor, MI (US); Dejan Teofilovic, Ann Arbor, MI (US); Zeljko Mladenovic, Orefield, PA (US); Aleksandra Rakic, Ann Arbor, MI (US); Joshua Stopek, Minneapolis, MN (US)

(73) Assignee: HistoSonics, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,050

(22) Filed: May 2, 2023

(65) Prior Publication Data
US 2023/0310901 A1 Oct. 5, 2023

Related U.S. Application Data

(63) Continuation of application No. 16/930,181, filed on Jul. 15, 2020, now Pat. No. 11,648,424, which is a
(Continued)

(51) Int. Cl.
*A61N 7/00* (2006.01)
*A61B 8/08* (2006.01)
*A61B 17/22* (2006.01)

(52) U.S. Cl.
CPC ............... *A61N 7/00* (2013.01); *A61B 8/085* (2013.01); *A61B 2017/22008* (2013.01); *A61N 2007/0039* (2013.01); *A61N 2007/0052* (2013.01)

(58) Field of Classification Search
CPC .............. A61N 7/00; A61N 2007/0039; A61N 2007/0052; A61B 8/085; A61B 2017/22008
See application file for complete search history.

(56) References Cited

U.S. PATENT DOCUMENTS 3,243,497 A 3/1966 Kendall et al.
3,679,021 A 7/1972 Goldberg et al.
(Continued)

FOREIGN PATENT DOCUMENTS

AU 2017222925 B2 11/2021
BR 112018017326 B1 12/2022
(Continued)

OTHER PUBLICATIONS

Maxwell et al.; U.S. Appl. No. 18/329,459 entitled "Histotripsy for thrombolysis," filed Jun. 5, 2023.
(Continued)

*Primary Examiner* — Shahdeep Mohammed
*Assistant Examiner* — Fikirte (Fiki) T Ashine
(74) *Attorney, Agent, or Firm* — Shay Glenn LLP

(57) ABSTRACT

A histotripsy therapy system configured for the treatment of tissue is provided, which may include any number of features. Provided herein are systems and methods that provide efficacious non-invasive and minimally invasive therapeutic, diagnostic and research procedures. In particular, provided herein are optimized systems and methods that provide targeted, efficacious histotripsy in a variety of different regions and under a variety of different conditions without causing undesired tissue damage to intervening/non-target tissues or structures.

20 Claims, 21 Drawing Sheets

Related U.S. Application Data continuation of application No. 16/698,587, filed on Nov. 27, 2019, now Pat. No. 11,813,484.

(60) Provisional application No. 62/772,473, filed on Nov. 28, 2018.

(56) References Cited

U.S. PATENT DOCUMENTS

| | | |
|---|---|---|
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,078,140 A | 1/1992 | Kwoh |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,492,126 A | 2/1996 | Hennige et al. |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,683,064 A | 11/1997 | Copeland et al. |
| 5,694,936 A | 12/1997 | Fujimoto et al. |
| 5,695,460 A | 12/1997 | Siegel et al. |
| 5,717,657 A | 2/1998 | Ruffa |
| 5,720,287 A | 2/1998 | Chapelon et al. |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,928,169 A | 7/1999 | Schitzle et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |

(56) References Cited

U.S. PATENT DOCUMENTS

| | | |
|---|---|---|
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Corl |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Corl |
| 11,026,591 B2 | 6/2021 | Burkett et al. |
| 11,040,140 B2 | 6/2021 | Unser et al. |
| 11,058,399 B2 | 7/2021 | Xu et al. |
| 11,071,522 B2 | 7/2021 | Hynynen et al. |
| 11,103,731 B2 | 8/2021 | Vortman et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,135,454 B2 | 10/2021 | Xu et al. |
| 11,141,063 B2 | 10/2021 | Kemp et al. |
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,748 B2 | 1/2022 | Burkett et al. |

(56) References Cited

U.S. PATENT DOCUMENTS

| | | |
|---|---|---|
| 11,224,349 B2 | 1/2022 | Davies et al. |
| 11,224,403 B2 | 1/2022 | Corl |
| 11,224,407 B2 | 1/2022 | Wrolstad et al. |
| 11,234,649 B2 | 2/2022 | Matsubara et al. |
| 11,246,533 B2 | 2/2022 | Henderson et al. |
| 11,246,565 B2 | 2/2022 | Corl |
| 11,253,225 B2 | 2/2022 | Hancock et al. |
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,906 B2 | 6/2022 | Castella et al. |
| 11,350,954 B2 | 6/2022 | De Cicco et al. |
| 11,364,042 B2 | 6/2022 | Maxwell et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,432,900 B2 | 9/2022 | Rakic et al. |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,517,291 B2 | 12/2022 | Kantor et al. |
| 11,547,389 B2 | 1/2023 | Shin et al. |
| 11,554,386 B2 | 1/2023 | Pernot et al. |
| 11,559,207 B2 | 1/2023 | Stigall et al. |
| 11,576,649 B2 | 2/2023 | Corl |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,384 B2 | 3/2023 | Nair et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,648,424 B2 * | 5/2023 | Cannata ............ A61B 34/30 601/2 |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,552 B2 | 6/2023 | Pasquino et al. |
| 11,684,342 B2 | 6/2023 | Groenland et al. |
| 11,684,807 B2 | 6/2023 | Vortman et al. |
| 11,701,134 B2 | 7/2023 | Maxwell et al. |
| 11,707,254 B2 | 7/2023 | Di Tullio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 11,759,174 B2 | 9/2023 | Saroha et al. |
| 11,766,237 B2 | 9/2023 | Anderson |
| 11,771,370 B2 | 10/2023 | Hynynen |
| 11,771,405 B2 | 10/2023 | Rhodes |
| 11,771,869 B2 | 10/2023 | Cicco |
| 11,806,167 B2 | 11/2023 | Burkett |
| 11,890,136 B2 | 2/2024 | Stigall et al. |
| 11,890,137 B2 | 2/2024 | Jenkins et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0164213 A1 | 8/2004 | Stephan |
| 2004/0236248 A1 | 11/2004 | Svedman |
| 2004/0243021 A1 | 12/2004 | Murphy et al. |
| 2004/0260214 A1 | 12/2004 | Echt et al. |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chomenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sar |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0254008 A1 | 10/2009 | Shields, Jr. |
| 2009/0287083 A1 | 11/2009 | Kushculey et al. |
| 2009/0306502 A1 | 12/2009 | Lacoste |

(56) References Cited

U.S. PATENT DOCUMENTS

| | | |
|---|---|---|
| 2010/0011845 A1 | 1/2010 | Laugharn et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0204578 A1 | 8/2010 | Schmidt et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0112400 A1 | 5/2011 | Emery et al. |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0245671 A1 | 10/2011 | Sato |
| 2011/0251528 A1 | 10/2011 | Canney et al. |
| 2011/0257524 A1 | 10/2011 | Gertner |
| 2011/0263967 A1 | 10/2011 | Bailey et al. |
| 2011/0270136 A1 | 11/2011 | Vitek et al. |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0041293 A1* | 2/2013 | Cain ............... A61B 8/13 601/2 |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1* | 4/2013 | Cain ............... A61N 7/00 601/2 |
| 2013/0144165 A1* | 6/2013 | Ebbini ............. G01S 7/52046 600/439 |
| 2013/0172739 A1 | 7/2013 | Paladini |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0303906 A1 | 11/2013 | Cain et al. |
| 2014/0030806 A1 | 1/2014 | Dudley et al. |
| 2014/0046181 A1 | 2/2014 | Benchimol et al. |
| 2014/0058293 A1 | 2/2014 | Hynynen et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1 | 4/2014 | Guo et al. |
| 2014/0128734 A1 | 5/2014 | Genstler et al. |
| 2014/0200489 A1 | 7/2014 | Behar et al. |
| 2014/0243664 A1 | 8/2014 | El-Sayed et al. |
| 2014/0330124 A1 | 11/2014 | Carol |
| 2014/0378832 A1 | 12/2014 | Sanghvi et al. |
| 2015/0011875 A1 | 1/2015 | Noordhoek et al. |
| 2015/0063668 A1 | 3/2015 | You et al. |
| 2015/0073261 A1 | 3/2015 | Kohler et al. |
| 2015/0151141 A1 | 6/2015 | Amal et al. |
| 2015/0190121 A1 | 7/2015 | Slayton et al. |
| 2015/0190659 A1 | 7/2015 | Kolher |
| 2015/0224347 A1 | 8/2015 | Barthe et al. |
| 2015/0080926 A1 | 9/2015 | Emery |
| 2015/0258352 A1 | 9/2015 | Lin et al. |
| 2015/0273246 A1* | 10/2015 | Darlington ............... A61N 7/02 601/3 |
| 2015/0297177 A1 | 10/2015 | Boctor et al. |
| 2016/0004933 A1 | 1/2016 | Hu et al. |
| 2016/0114194 A1 | 4/2016 | Gertner |
| 2016/0120572 A1 | 5/2016 | Lee |
| 2016/0135782 A1* | 5/2016 | Chen .................. A61B 8/0875 600/440 |
| 2016/0151618 A1 | 6/2016 | Powers et al. |
| 2016/0184614 A1 | 6/2016 | Matula et al. |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0232277 A1 | 8/2017 | Hall et al. |
| 2017/0281983 A1 | 10/2017 | Marquet et al. |
| 2018/0000444 A1 | 1/2018 | Dayton et al. |
| 2018/0028841 A1 | 2/2018 | Konofagou et al. |
| 2018/0064412 A1 | 3/2018 | Messas et al. |
| 2018/0161086 A1 | 6/2018 | Davalos et al. |
| 2018/0169444 A1 | 6/2018 | Averkiou et al. |
| 2018/0206816 A1 | 7/2018 | Prus et al. |
| 2018/0236271 A1 | 8/2018 | Tanter et al. |
| 2018/0317884 A1 | 11/2018 | Chapelon et al. |
| 2019/0000422 A1 | 1/2019 | West et al. |
| 2019/0023804 A1 | 1/2019 | Onik et al. |
| 2019/0275353 A1 | 9/2019 | Cannata et al. |
| 2019/0282294 A1 | 9/2019 | Davalos et al. |
| 2020/0010575 A1 | 1/2020 | Hode et al. |
| 2020/0055085 A1 | 2/2020 | Taffler |
| 2020/0078608 A1 | 3/2020 | Maxwell et al. |
| 2020/0107843 A1 | 4/2020 | Goertz et al. |
| 2020/0164231 A1* | 5/2020 | Cannata .................. A61N 7/00 |
| 2020/0253550 A1 | 8/2020 | Nair |
| 2020/0260964 A1 | 8/2020 | Collins et al. |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0353293 A1 | 11/2020 | Khokhlova et al. |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0008394 A1 | 1/2021 | Cain et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0161398 A1 | 6/2021 | Millett et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0252313 A1 | 8/2021 | Xu et al. |
| 2021/0353161 A1 | 11/2021 | Merritt et al. |
| 2021/0386451 A1 | 12/2021 | Escudero et al. |
| 2021/0401400 A1 | 12/2021 | Sheehan et al. |
| 2022/0008036 A1 | 1/2022 | Gulsen et al. |
| 2022/0043143 A1 | 2/2022 | Prus et al. |

(56) References Cited

U.S. PATENT DOCUMENTS

| | | | |
|---|---|---|---|
| 2022/0079563 A1 | 3/2022 | Kemp | |
| 2022/0087640 A1 | 3/2022 | Minas et al. | |
| 2022/0166462 A1 | 5/2022 | Deurenberg et al. | |
| 2022/0168470 A1 | 6/2022 | Ricotti et al. | |
| 2022/0196771 A1 | 6/2022 | Zur et al. | |
| 2022/0203139 A1 | 6/2022 | Shapira | |
| 2022/0219019 A1 | 7/2022 | Xu et al. | |
| 2022/0233890 A1 | 7/2022 | Hynynen et al. | |
| 2022/0257329 A1 | 8/2022 | Stigall et al. | |
| 2022/0280233 A1 | 9/2022 | Park et al. | |
| 2022/0296211 A1 | 9/2022 | Saroha et al. | |
| 2022/0346756 A1 | 11/2022 | Chen | |
| 2023/0038498 A1 | 2/2023 | Xu et al. | |
| 2023/0038543 A1 | 2/2023 | Minas et al. | |
| 2023/0042834 A1 | 2/2023 | Henderson et al. | |
| 2023/0050732 A1 | 2/2023 | Hancock et al. | |
| 2023/0061534 A1 | 3/2023 | Stopek | |
| 2023/0218930 A1 | 7/2023 | Stopek et al. | |

FOREIGN PATENT DOCUMENTS

| | | |
|---|---|---|
| CA | 3073552 A1 | 3/2019 |
| CA | 3101381 A1 | 11/2019 |
| CA | 3055856 A1 | 4/2020 |
| CA | 3153080 A1 | 4/2021 |
| CA | 2910561 C | 7/2021 |
| CA | 2908740 C | 10/2021 |
| CA | 2980976 C | 3/2023 |
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 106999076 B | 8/2017 |
| CN | 109185113 A | 1/2019 |
| CN | 109219415 A | 1/2019 |
| CN | 109689160 A | 4/2019 |
| CN | 111565642 A | 8/2020 |
| CN | 111655337 A | 9/2020 |
| CN | 111699022 A | 9/2020 |
| CN | 111712300 A | 9/2020 |
| CN | 111712301 A | 9/2020 |
| CN | 106999053 B | 10/2020 |
| CN | 107660137 B | 10/2020 |
| CN | 111757769 A | 10/2020 |
| CN | 112204412 A | 1/2021 |
| CN | 112236195 A | 1/2021 |
| CN | 106661535 B | 3/2021 |
| CN | 112533673 A | 3/2021 |
| CN | 112566694 A | 3/2021 |
| CN | 106999054 B | 5/2021 |
| CN | 106793997 B | 6/2021 |
| CN | 107530049 B | 6/2021 |
| CN | 112912011 A | 6/2021 |
| CN | 112912012 A | 6/2021 |
| CN | 112912013 A | 6/2021 |
| CN | 112969413 A | 6/2021 |
| CN | 112996445 A | 6/2021 |
| CN | 113167877 A | 7/2021 |
| CN | 113196080 A | 7/2021 |
| CN | 109196369 B | 8/2021 |
| CN | 109200484 B | 8/2021 |
| CN | 113316419 A | 8/2021 |
| CN | 113329788 A | 8/2021 |
| CN | 109640830 B | 10/2021 |
| CN | 113473917 A | 10/2021 |
| CN | 113507946 A | 10/2021 |
| CN | 113518588 A | 10/2021 |
| CN | 113705586 A | 11/2021 |
| CN | 110662575 B | 12/2021 |
| CN | 113905666 A | 1/2022 |
| CN | 114222536 A | 3/2022 |
| CN | 114423362 A | 4/2022 |
| CN | 110248606 B | 6/2022 |
| CN | 115227992 A | 10/2022 |
| CN | 109843181 B | 11/2022 |
| CN | 109091768 B | 3/2023 |
| CN | 115779285 A | 3/2023 |
| CN | 115779287 A | 3/2023 |
| CN | 115813438 A | 3/2023 |
| CN | 111032157 B | 4/2023 |
| CN | 110958858 B | 5/2023 |
| CN | 116172611 A | 5/2023 |
| CN | 111655337 B | 6/2023 |
| CN | 109416908 B | 7/2023 |
| CN | 107529989 B | 8/2023 |
| CN | 111372522 B | 8/2023 |
| CN | 116617589 A | 8/2023 |
| CN | 112236195 B | 9/2023 |
| CN | 109416907 B | 10/2023 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| EP | 2934308 B1 | 10/2015 |
| EP | 2934309 B1 | 10/2015 |
| EP | 3097180 B1 | 11/2016 |
| EP | 2759003 B1 | 8/2020 |
| EP | 3558457 A4 | 8/2020 |
| EP | 3700629 A1 | 9/2020 |
| EP | 3218829 B1 | 10/2020 |
| EP | 3229688 B1 | 10/2020 |
| EP | 3723857 A1 | 10/2020 |
| EP | 2887989 B1 | 2/2021 |
| EP | 3777689 A1 | 2/2021 |
| EP | 2938253 B1 | 3/2021 |
| EP | 3076864 B1 | 3/2021 |
| EP | 2802276 B1 | 4/2021 |
| EP | 2809221 B1 | 4/2021 |
| EP | 3801761 A1 | 4/2021 |
| EP | 3801762 A2 | 4/2021 |
| EP | 3801763 A1 | 4/2021 |
| EP | 2967369 B1 | 5/2021 |
| EP | 2967488 B1 | 6/2021 |
| EP | 3184048 B1 | 6/2021 |
| EP | 2967370 B1 | 9/2021 |
| EP | 3482390 B1 | 9/2021 |
| EP | 3870067 A1 | 9/2021 |
| EP | 3870069 A1 | 9/2021 |
| EP | 3876843 A1 | 9/2021 |
| EP | 2931130 B1 | 10/2021 |
| EP | 2934304 B1 | 10/2021 |
| EP | 3887843 A1 | 10/2021 |
| EP | 3888534 A1 | 10/2021 |
| EP | 3895604 A1 | 10/2021 |
| EP | 3897391 A1 | 10/2021 |
| EP | 3229672 B1 | 11/2021 |
| EP | 3902603 A1 | 11/2021 |
| EP | 3903672 A1 | 11/2021 |
| EP | 2964096 B1 | 12/2021 |
| EP | 3930776 A1 | 1/2022 |
| EP | 3545829 B1 | 3/2022 |
| EP | 3060129 B1 | 4/2022 |
| EP | 3986296 A1 | 4/2022 |
| EP | 2914166 B1 | 5/2022 |
| EP | 3229674 B1 | 5/2022 |
| EP | 2779907 B1 | 6/2022 |
| EP | 3102098 B1 | 6/2022 |
| EP | 2965263 B1 | 7/2022 |

(56) References Cited

FOREIGN PATENT DOCUMENTS

| | | | |
|---|---|---|---|
| EP | 2726152 B1 | 8/2022 |
| EP | 4041387 A1 | 8/2022 |
| EP | 4042936 A1 | 8/2022 |
| EP | 3298959 B2 | 9/2022 |
| EP | 2931131 B1 | 11/2022 |
| EP | 2938268 B1 | 11/2022 |
| EP | 3581103 B1 | 11/2022 |
| EP | 3091905 B1 | 12/2022 |
| EP | 4098203 A1 | 12/2022 |
| EP | 2950737 B1 | 1/2023 |
| EP | 3057496 B1 | 1/2023 |
| EP | 2869804 B1 | 2/2023 |
| EP | 2938265 B1 | 2/2023 |
| EP | 3024403 B1 | 3/2023 |
| EP | 4151156 A1 | 3/2023 |
| EP | 2938271 B1 | 4/2023 |
| EP | 4179995 A2 | 5/2023 |
| EP | 3171764 B1 | 6/2023 |
| EP | 2931132 B1 | 7/2023 |
| EP | 3229695 B1 | 7/2023 |
| EP | 4226864 A1 | 8/2023 |
| EP | 4230121 A2 | 8/2023 |
| EP | 4230146 A1 | 8/2023 |
| EP | 4233972 A2 | 8/2023 |
| EP | 2866733 B1 | 9/2023 |
| EP | 3870069 B1 | 9/2023 |
| EP | 3484371 B1 | 10/2023 |
| EP | 3658037 B1 | 10/2023 |
| EP | 3685874 B1 | 10/2023 |
| EP | 3870070 B1 | 10/2023 |
| EP | 2938255 B1 | 11/2023 |
| EP | 3229906 B1 | 11/2023 |
| EP | 3764914 B1 | 11/2023 |
| EP | 3903672 B1 | 11/2023 |
| EP | 4272654 A2 | 11/2023 |
| EP | 4275609 A2 | 11/2023 |
| EP | 3908195 B1 | 2/2024 |
| ES | 2774069 T3 | 7/2020 |
| ES | 2819552 T3 | 4/2021 |
| ES | 2829822 T3 | 6/2021 |
| GB | 2099582 A | 12/1982 |
| HK | 1245715 B | 1/2021 |
| IL | 254768 A | 5/2021 |
| IL | 261285 B | 2/2022 |
| IN | 202117039853 A | 12/2021 |
| IN | 387413 B | 1/2022 |
| IN | 445766 B | 8/2023 |
| JP | 60-80779 A | 5/1985 |
| JP | 61-196718 A | 8/1986 |
| JP | 02-215451 A | 8/1990 |
| JP | H0422351 A | 1/1992 |
| JP | 06-197907 A | 7/1994 |
| JP | 07-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | 10-512477 A | 12/1998 |
| JP | 2000300559 A | 10/2000 |
| JP | 2003510159 A | 3/2003 |
| JP | 2004505660 A | 2/2004 |
| JP | 2004249106 A | 9/2004 |
| JP | 2005167058 A | 6/2005 |
| JP | 2006511265 A | 4/2006 |
| JP | 2007144225 A | 6/2007 |
| JP | 2007520307 A | 7/2007 |
| JP | 2010019554 A | 1/2010 |
| JP | 2010029650 A | 2/2010 |
| JP | 2010204068 A | 9/2010 |
| JP | 2013538097 A | 10/2013 |
| JP | 2004512502 A | 4/2014 |
| JP | 2015519970 A | 7/2015 |
| JP | 2016508808 A | 3/2016 |
| JP | 2020525167 A | 8/2020 |
| JP | 2020525168 A | 8/2020 |
| JP | 2020525169 A | 8/2020 |
| JP | 6785554 B2 | 10/2020 |
| JP | 6789944 B2 | 11/2020 |
| JP | 2020534077 A | 11/2020 |
| JP | 2020195788 A | 12/2020 |
| JP | 2020535895 A | 12/2020 |
| JP | 6832958 B2 | 2/2021 |
| JP | 6835719 B2 | 2/2021 |
| JP | 6838057 B2 | 3/2021 |
| JP | 6849592 B2 | 3/2021 |
| JP | 2021510104 A | 4/2021 |
| JP | 6896719 B2 | 6/2021 |
| JP | 6934933 B2 | 9/2021 |
| JP | 6951560 B2 | 10/2021 |
| JP | 6979633 B2 | 12/2021 |
| JP | 6980696 B2 | 12/2021 |
| JP | 7012726 B2 | 1/2022 |
| JP | 2022500092 A | 1/2022 |
| JP | 2022500093 A | 1/2022 |
| JP | 2022501080 A | 1/2022 |
| JP | 2022504159 A | 1/2022 |
| JP | 2022509389 A | 1/2022 |
| JP | 2022509391 A | 1/2022 |
| JP | 2022509392 A | 1/2022 |
| JP | 2022509393 A | 1/2022 |
| JP | 2022509395 A | 1/2022 |
| JP | 2022509401 A | 1/2022 |
| JP | 2022509453 A | 1/2022 |
| JP | 2022510217 A | 1/2022 |
| JP | 7019679 B2 | 2/2022 |
| JP | 7026118 B2 | 2/2022 |
| JP | 2022514272 A | 2/2022 |
| JP | 2022515488 A | 2/2022 |
| JP | 2022516078 A | 2/2022 |
| JP | 7053500 B2 | 4/2022 |
| JP | 2022526104 A | 5/2022 |
| JP | 2022527043 A | 5/2022 |
| JP | 2022095785 A | 6/2022 |
| JP | 7171645 B2 | 11/2022 |
| JP | 7171663 B2 | 11/2022 |
| JP | 7175640 B2 | 11/2022 |
| JP | 7232204 B2 | 3/2023 |
| JP | 7239466 B2 | 3/2023 |
| JP | 7265525 B2 | 4/2023 |
| JP | 2023071859 A | 5/2023 |
| JP | 7299992 B2 | 6/2023 |
| JP | 7302936 B2 | 7/2023 |
| JP | 7304344 B2 | 7/2023 |
| JP | 7321162 B2 | 8/2023 |
| JP | 7325430 B2 | 8/2023 |
| JP | 7340594 B2 | 9/2023 |
| JP | 7346293 B2 | 9/2023 |
| JP | 7352561 B2 | 9/2023 |
| JP | 7358391 B2 | 10/2023 |
| JP | 7359765 B2 | 10/2023 |
| JP | 7370386 B2 | 10/2023 |
| JP | 2023162327 A | 11/2023 |
| JP | 2024020483 A | 2/2024 |
| KR | 102574559 B1 | 9/2023 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |
| WO | WO2011/040054 A1 | 7/2011 |
| WO | WO2011/092683 A1 | 8/2011 |
| WO | WO2011/154654 A2 | 12/2011 |
| WO | WO2014/008594 A1 | 1/2014 |
| WO | WO2014/071386 A1 | 5/2014 |
| WO | WO2015/000953 A1 | 1/2015 |
| WO | WO2015/031532 A1 | 3/2015 |
| WO | WO2018/149671 A1 | 8/2018 |
| WO | WO2019/081329 A1 | 5/2019 |
| WO | WO2019/122941 A1 | 6/2019 |
| WO | WO2020/087049 A1 | 4/2020 |
| WO | WO2020/217098 A2 | 10/2020 |
| WO | WO2020/237382 A1 | 12/2020 |
| WO | WO2020/245660 A1 | 12/2020 |
| WO | WO2021/014221 A1 | 1/2021 |
| WO | WO2021/032887 A1 | 2/2021 |

(56) References Cited

FOREIGN PATENT DOCUMENTS

| WO | WO2021/069216 A1 | 4/2021 |
|---|---|---|
| WO | WO2021/069971 A1 | 4/2021 |
| WO | WO2021/089810 A1 | 5/2021 |
| WO | WO2021/105358 A1 | 6/2021 |

OTHER PUBLICATIONS

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bak; Rapid protytyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon.com/dgdl/infineon+-+Application+Note+-+PowerMOSFETs+-+600V+CoolMOS%E284%A2+-+CP+Most+be neficial+use+of+superjunction+technologie+devices.pdf?folderid=db3a304412b407950112b408e8c90004&fileId=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Dovedi et al.; Acquired Resistance to Fractionated Radiotherapy Can Be Overcome by Concurrent PD-L1 Blockade; Cancer Research; 74(19); pp. 5458-5468; Oct. 1, 2014.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter: Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.

(56) References Cited

OTHER PUBLICATIONS

Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011 [retrieved on Jan. 28, 2014] from: (http://web.archive.org/web/20110720091822/http://www.histotripsy.umich.edu/index.html>.entiredocument) Jul. 2011.

(56) References Cited

OTHER PUBLICATIONS

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_utrasound&oldid=515340960) on Jan. 12, 2018.

Wu et al.; Mechanism and dynamics of hydrodynamic-acoustic cavitation (HAC); Ultrasonics sonochemistry; vol. 49., pp. 89-96; Dec. 1, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Rakic et al.; U.S. Appl. No. 17/929,951 entitled "Articulating arm limiter for cavitational ultrasound therapy system," filed Sep. 6, 2022.

Hall et al.; U.S. Appl. No. 18/043,251 entitled "Ultrasound transducer with transmit-receive capability for histotripsy," filed Feb. 27, 2023.

Xu et al.; U.S. Appl. No. 18/744,867 entitled "Transcranial mr-guided histotripsy systems and methods," filed Mar. 10, 2023.

Cannata et al.; U.S. Appl. No. 18/311,045 entitled "Histotripsy systems and methods," filed May 2, 2023.

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Cannata et al.; U.S. Appl. No. 18/464,877 entitled "Histotripsy systems and methods," filed Sep. 11, 2023.

Cannata et al.; U.S. Appl. No. 18/464,721 entitled "Histotripsy systems and methods," filed Sep. 11, 2023.

Gateau et al.; Transcranial ultrasonic therapy based on time reversal of acoustically induced cavitation bubble signature. IEEE Transactions on Biomedical Engineering; 57(1); pp. 134-144; Sep. 18, 2009.

\* cited by examiner

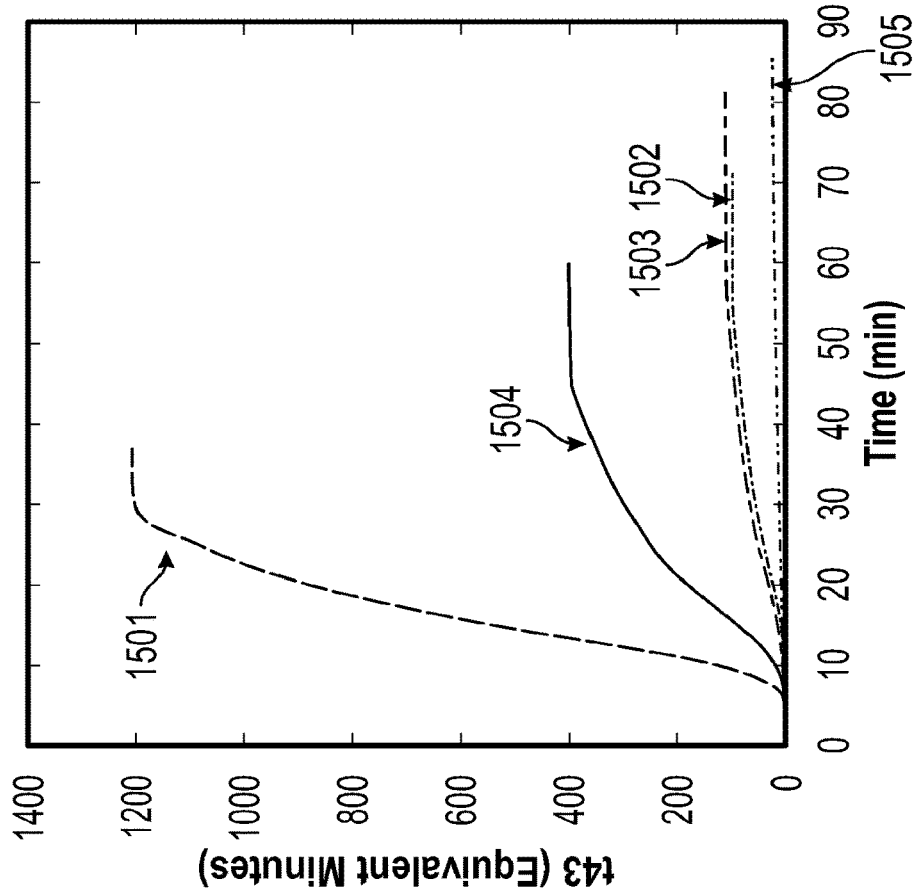
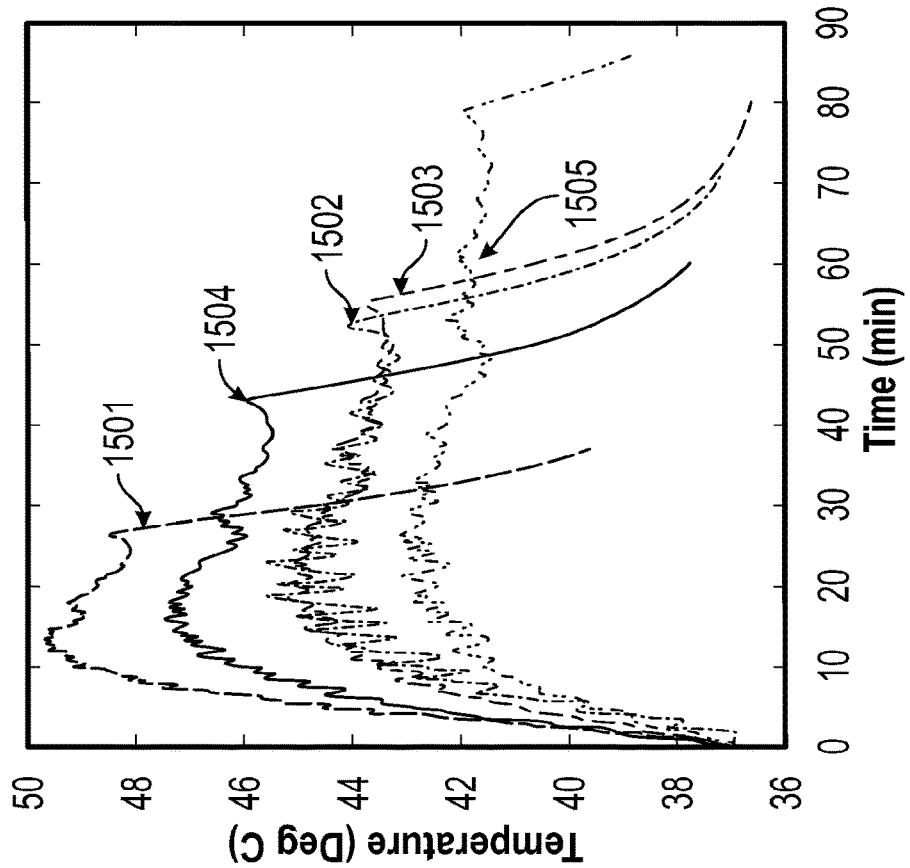
FIG. 15B
FIG. 15A

HISTOTRIPSY SYSTEMS AND METHODS

CROSS REFERENCE TO RELATED APPLICATIONS

This application is a continuation of U.S. application Ser. No. 16/930,181, filed Jul. 15, 2020, which is a continuation of U.S. application Ser. No. 16/698,587, filed Nov. 27, 2019, which application claims the benefit of U.S. Provisional Application No. 62/772,473, filed Nov. 28, 2018, titled "HISTOTRIPSY SYSTEMS AND METHODS", both of which are incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel histotripsy systems configured to produce acoustic cavitation, methods, devices and procedures for the minimally and non-invasive treatment of healthy, diseased and/or injured tissue. The histotripsy systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Many medical conditions require invasive surgical interventions. Invasive procedures often involve incisions, trauma to muscles, nerves and tissues, bleeding, scarring, trauma to organs, pain, need for narcotics during and following procedures, hospital stays, and risks of infection. Non-invasive and minimally invasive procedures are often favored, if available, to avoid or reduce such issues. Unfortunately, non-invasive and minimally invasive procedures may lack the precision, efficacy or safety required for treatment of many types of diseases and conditions. Enhanced non-invasive and minimally invasive procedures are needed, preferably not requiring ionizing or thermal energy for therapeutic effect.

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, and high-intensity focused ultrasound (HIFU), Histotripsy relies on the mechanical action of cavitation for tissue destruction.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 15A-15B illustrate the thermal profiles resulting from the five treatment schemes used to investigate the implementation of cooling steps during volume treatment.

SUMMARY OF THE DISCLOSURE

Figure 1A:
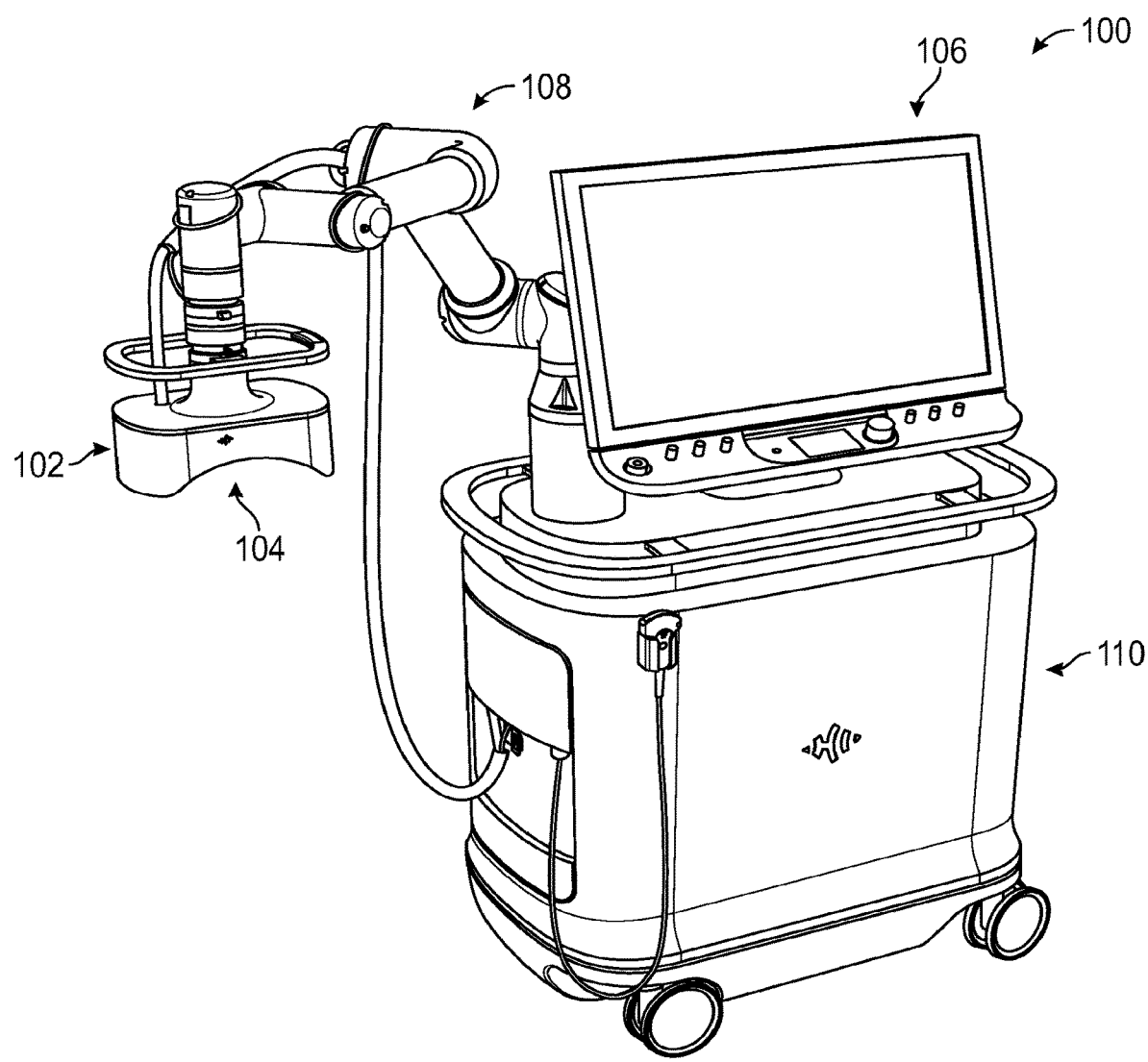
FIGS. 1A-1B illustrate an ultrasound imaging and therapy system.

Histotripsy produces tissue fractionation through dense energetic bubble clouds generated by short, high-pressure, ultrasound pulses. When using pulses shorter than 2 cycles, the generation of these energetic bubble clouds only depends on where the peak negative pressure (P−) exceeds an intrinsic threshold for inducing cavitation in a medium (typically 26-30 MPa in soft tissue with high water content).

A method of treating tissue is provided, comprising the steps of transmitting ultrasound pulses into a first test location with at least one ultrasound transducer, determining a first cavitation threshold at the first test location, transmitting ultrasound pulses into a second test location with the at least one ultrasound transducer, determining a second cavitation threshold at the second test location, adjusting a first driving voltage and/or PRF of the at least one transducer based on the first cavitation threshold, transmitting ultrasound pulses into the first test location with the at least one ultrasound transducer at the first adjusted driving voltage and/or PRF to generate cavitation at the first test location, adjusting a second driving voltage and/or PRF of the at least one transducer based on the second cavitation threshold and transmitting ultrasound pulses into the second test location with the at least one ultrasound transducer at the second adjusted driving voltage and/or PRF to generate cavitation at the second test location.

In some embodiments, the method further comprises repeating the steps at three or more test locations in the tissue.

In other embodiments, the method further comprises repeating the steps at six or more test locations in the tissue. The six or more test locations may be positioned in cubic coordinates around a center of said target location.

In some embodiments, the method further comprises repeating the steps at seven or more test locations in the tissue. Six target locations may be positioned in cubic coordinates spaced around a central test location.

In some embodiments, the method further comprises determining a cavitation threshold for a third test location located between the first and second test locations by extrapolating a cavitation threshold based on the cavitation thresholds of the first and second test locations.

In other embodiments, the method further comprises interpolating required drive amplitudes for the first test location, the second test location, and the third test location to ensure that each of the cavitation thresholds is achieved. The first and second test locations may be positioned near an outer boundary of the tissue.

In some embodiments, the tissue comprises a tumor volume. In other embodiments, the tissue comprises a tumor volume and a margin around the tumor volume.

In some embodiments, the first and second test locations are two or more tumors.

In some embodiments, the method further comprises positioning the first and second test locations on the tissue in a graphical user interface.

In some embodiments, the steps are performed automatically without intervention by a user.

In some embodiments, the method further comprises making a depth measurement at the first and second test locations.

In other embodiments, the method further comprises determining a maximum amount of energy that may be applied to the first test location without generating undesired damage to the first test location or surrounding intervening tissue.

In some embodiments, the method further comprises determining a threshold of energy that may be applied to the first location without generating undesired damage to the first test location or surrounding intervening tissue.

In alternative embodiments, the method further comprises positioning the at least one transducer 3 cm or more from the tissue.

In some embodiments, the method further comprises positioning the at least one transducer 5 cm or more from the tissue.

In other embodiments, the method further comprises positioning the at least one transducer 10 cm or more from the tissue.

In some embodiments, one or more bone structures are located between the at least one transducer and tissue.

In some examples, the ultrasound pulses comprise histotripsy pulses.

A method of treating tissue with a pulse repetition frequency (PRF) of 400 Hz or greater to generate acoustic cavitation is provided, comprising the steps of transmitting ultrasound pulses into a first test location with at least one ultrasound transducer, determining a first cavitation threshold at the first test location, transmitting ultrasound pulses into a second test location with the at least one ultrasound transducer, determining a second cavitation threshold at the second test location, adjusting a first driving voltage and/or pulse repetition frequency of the at least one transducer based on the first cavitation threshold, transmitting ultrasound pulses into the first test location with the at least one ultrasound transducer at the first adjusted driving voltage to generate cavitation at the first test location, adjusting a second driving voltage and/or pulse repetition frequency of the at least one transducer based on the second cavitation threshold, and transmitting ultrasound pulses into the second test location with the at least one ultrasound transducer at the second adjusted driving voltage to generate cavitation at the second test location.

In some examples, the PRF is between 400 to 900 Hz, between 600 to 900 Hz, between 500 to 700 Hz, or the PRF is 600 Hz.

In some embodiments, the method further comprises implementing a test protocol that identifies treatment power thresholds at two or more test locations in the tissue.

In some embodiments, the method further comprises implementing a treatment protocol that selects a power of one or more treatment locations within the tissue based on the test protocol.

In other embodiments, the method further comprises transmitting the ultrasound pulses with a robot.

In some embodiments, the method further comprises destroying cells in a target tissue with the transmitted pulses. In additional embodiments, the method further comprises destroying cells in a target tissue without damaging critical tissue structures. The critical tissue structures may be selected from the group consisting of blood vessels, bile ducts, collecting systems, organ capsules and visceral structures.

A method of treating tissue with ultrasound energy is provided, comprising the steps of delivering ultrasound pulses into a target tissue with one or more ultrasound transducers to generate acoustic cavitation in the target tissue, adjusting a power and a position of the one or more ultrasound transducers to generate bubble clouds at a plurality of different locations in the target tissue over a plurality of time periods to treat at least two locations located in non-contiguous regions of the target tissue in sequential time periods.

In some embodiments, the method further comprises forming a plurality of treatment lines that span the target tissue. In some examples, the plurality of treatment lines comprises a first line that spans from a first side of the target tissue to a second side of the target tissue. In other examples, the plurality of treatment lines further proceeds along a second line from the first side of said target tissue to the second side of the target tissue.

In some embodiments, the plurality of treatment lines further proceeds along third and subsequent lines, each starting from the first side of the target tissue to the second side of the target tissue.

In some embodiments, the first side comprises a top region of the target tissue located closest to the one or more ultrasound transducers and the second side comprises a bottom region of the target tissue located most distal to the one or more ultrasound transducers.

In some embodiments, the method further comprises identifying treatment power thresholds at two or more test locations in said target tissue.

In some embodiments, the method further comprises adjusting a power level of the one or more transducers based on the treatment power thresholds.

In other embodiments, the method further comprises performing a depth measurement at the two or more test locations.

In some embodiments, the method further comprises positioning the one or more ultrasound transducers with a robotic arm with three or more degrees of freedom.

In additional embodiments, the method further comprises positioning the one or more ultrasound transducers with a robotic arm wherein three or more degrees of freedom is six degrees of freedom.

In some embodiments, the method further comprises displaying real-time visualization of the bubble cloud at first and subsequent locations in the treatment pattern during the treatments.

In other embodiments, the method further comprises displaying a status of the treatment and position of the bubble cloud in the planned treatment pattern, wherein status includes information derived from a location, position, percentage of treatment completion, percentage of treatment remaining, and time. In some embodiments, this can include displaying a combination of real-time visualization and CT and/or MRI images.

A system is provided, comprising one or more ultrasound transducers configured to generate acoustic cavitation in a tissue at a target location, and one or more computer processors configured to control power and position of said ultrasound transducers, wherein said one or more processors are configured to implement a treatment pattern in the one or more ultrasound transducers that generates bubble clouds at a plurality of different locations in the target tissue over a plurality of time periods, wherein at least two of said locations are treated in sequential time periods are located in contiguous columns of the target tissue.

In some embodiments, the treatment pattern comprises a plurality of treatment columns that span said target location.

In other embodiments, the treatment pattern proceeds along a first column location to said starting position of a second column location.

In some examples, the treatment pattern further proceeds along a second column from said first column location within said target location to a third column starting position within said target location.

In other embodiments, the treatment pattern further proceeds along third and subsequent columns of said target location.

In some embodiments, the treatment pattern comprises a radial spiral pattern. The radial spiral pattern can be formed from the inner locations to outer locations.

In some embodiments, the one or more processors are further configured to run implement a test protocol that identifies treatment power thresholds at two or more test locations in said target location. Power applied in said treatment pattern can be selected using information obtained from said test protocol. The test protocol can further include a depth measurement.

In some examples, the system is configured to dynamically control treatment parameters at a plurality of treatment locations in the target tissue. In other embodiments, the system is further configured to comprise a robotic arm with three or more degrees of freedom to control position of said one or more transducers. Additionally, the system can be further configured to comprise a robotic arm wherein three or more degrees of freedom is six degrees of freedom to control position of said one or more transducers.

The system can be further configured to display real-time visualization of the bubble cloud at first and subsequent locations in the treatment pattern during the treatment, as displayed to the user in one or more system user interfaces.

In some embodiments, the system is configured to display the status of the treatment and position of the bubble cloud in the planned treatment pattern, wherein status includes information derived from a list including location, position, percentage of treatment completion, percentage of treatment remaining, and time.

A system is provided, comprising one or more ultrasound transducers configured to generate acoustic cavitation in a tissue at a target location, and one or more computer processors configured to control power and position of said ultrasound transducers, wherein the one or more processors are configured to adjust energy delivery from the one or more ultrasound transducers based on treatment specific parameters accounting for tissue variation in the target location and/or obstructions located between the transducers and the target location.

The energy adjustment can comprise a timing of energy delivery, or an amplitude of energy delivery, or a selection of a cooling time period.

In some examples, the timing of energy delivery comprises application of energy for a first time period at a first location in the target tissue and for a second, different time period at a second location in the target tissue. Alternatively, the timing of energy delivery comprises application of energy for a first amplitude at a first location in the target tissue and for a second, different amplitude at a second location in the target tissue. In some examples, the timing of energy delivery comprises application of energy for a third or more time period, at a corresponding third or more location, in the target tissue.

In one embodiment, the amplitude of energy delivery comprises application of energy for a third or more amplitude, at a corresponding third or more location, in the target tissue.

In some examples, the system comprises one or more user interfaces for receiving user provided input of said treatment specific parameters.

In one embodiment, treatment specific parameters are pulled from a look-up table that contains energy delivery information indexed against a target tissue depth. The target tissue depth can be determined based on a distance between the center of the target tissue and a body wall located between the target tissue and the said one or more transducers. In some embodiments, the look-up table is specific for said one or more transducers. In other embodiments, the look-up table is specific for said target tissue type.

A method of treating a target tissue with ultrasound energy is also provided, wherein the target tissue comprises a first tissue component and a second tissue component, the method comprising the steps of delivering ultrasound pulses into the target tissue to form cavitation in the first tissue component but not the second tissue component.

An autotransforming inductive driver configured to excite ultrasound transducers is also provided, comprising an IGBT transistor, an oscillating circuit configured to temporarily store energy in a magnetic field when the IGBT transistor is excited with a single pulse, wherein the oscillating circuit includes an inductor with a tap that is positioned along a length of the inductor to increase a voltage generated across the inductor.

A method of treating a target tissue volume with an ultrasound system, comprising determining a depth of the target tissue volume, determining a total treatment time, positioning a focus of the ultrasound system on the target tissue volume, selecting a drive voltage, for the selected drive voltage, automatically determining in the ultrasound system a first percentage of the total treatment time for which ultrasound pulses are to be delivered to the target tissue volume and a second percentage of the total treatment time for which no ultrasound pulses are to be delivered to the target tissue volume, and initiating a pulse sequence in the ultrasound system configured to deliver ultrasound pulses to the target tissue for the first percentage of the total treatment time.

In some examples, determining the first percentage and the second percentage further comprises using a lookup table based on the drive voltage and the depth.

In one embodiment, the drive voltage and the depth of the target tissue volume are used to determine the first percentage and the second percentage.

In some embodiments, the lookup table provides a cooling coefficient used to determine a ratio between the first percentage and the second percentage.

In some examples, the first percentage comprises 50% and the second percentage comprises 50%, the first percentage comprises 33% and the second percentage comprises 67%, the first percentage comprises 25% and the second percentage comprises 75%, the first percentage comprises 20% and the second percentage comprises 80%, the first percentage comprises 16% and the second percentage comprises 84%.

In one embodiment, delivering the ultrasound pulses to the target tissue for the first percentage of the total treatment time prevents unwanted damage to surrounding tissues.

DETAILED DESCRIPTION

Provided herein are systems and methods that provide efficacious non-invasive and minimally invasive therapeutic, diagnostic and research procedures. In particular, provided herein are optimized systems and methods that provide targeted, efficacious histotripsy in a variety of different regions and under a variety of different conditions without causing undesired tissue damage to intervening/non-target tissues or structures.

Balancing desired tissue destruction in target regions with the avoidance of damage to non-target regions presents a technical challenge. This is particularly the case where time efficient procedures are desired. Conditions that provide fast, efficacious tissue destruction tend to cause undue heating in non-target tissues. Under heating can be avoided by reducing energy or slower delivery of energy, both of which run contrary to the goals of providing a fast and efficacious destruction of target tissue. Provided herein are a number of technologies that individually and collectively allow for fast, efficacious target treatment without undesired damage to non-target regions.

The system, methods and devices of the disclosure may be used for the minimally or non-invasive acoustic cavitation and treatment of healthy, diseased and/or injured tissue, including in extracorporeal, percutaneous, endoscopic, laparoscopic, and/or as integrated into a robotically-enabled medical system and procedures. As will be described below, the histotripsy system may include various electrical, mechanical and software sub-systems, including a Cart, Therapy, Integrated Imaging, Robotics, Coupling and Software. The system also may comprise various Other Components, Ancillaries and Accessories, including but not limited to patient surfaces, tables or beds, computers, cables and connectors, networking devices, power supplies, displays, drawers/storage, doors, wheels, illumination and lighting and various simulation and training tools, etc. All systems, methods and means creating/controlling/delivering histotripsy are considered to be a part of this disclosure, including new related inventions disclosed herein.

In one embodiment, the histotripsy system is configured as a mobile therapy cart, which further includes a touchscreen display with an integrated control panel with a set of physical controls, a robotic arm, a therapy head positioned on the distal end of the robot, a patient coupling system and software to operate and control the system.

The mobile therapy cart architecture can comprise internal components, housed in a standard rack mount frame, including a histotripsy therapy generator, high voltage power supply, transformer, power distribution, robot controller, computer, router and modem, and an ultrasound imaging engine. The front system interface panel can comprise input/output locations for connectors, including those specifically for two ultrasound imaging probes (handheld and probe coaxially mounted in the therapy transducer), a histotripsy therapy transducer, AC power and circuit breaker switches, network connections and a foot pedal. The rear panel of the cart can comprise air inlet vents to direct airflow to air exhaust vents located in the side, top and bottom panels. The side panels of the cart include a holster and support mechanism for holding the handheld imaging probe. The base of the cart can be comprised of a cast base interfacing with the rack mounted electronics and providing an interface to the side panels and top cover. The base also includes four recessed casters with a single total locking mechanism. The top cover of the therapy cart can comprise the robot arm base and interface, and a circumferential handle that follows the contour of the cart body. The cart can have inner mounting features that allow technician access to cart components through access panels.

The touchscreen display and control panel may include user input features including physical controls in the form of six dials, a space mouse and touchpad, an indicator light bar, and an emergency stop, together configured to control imaging and therapy parameters, and the robot. The touchscreen support arm is configured to allow standing and seated positions, and adjustment of the touchscreen orientation and viewing angle. The support arm further can comprise a system level power button and USB and ethernet connectors.

The robotic arm can be mounted to the mobile therapy cart on arm base of sufficient height to allow reach and ease of use positioning the arm in various drive modes into the patient/procedure work space from set up, through the procedure, and take down. The robotic arm can comprise six degrees of freedom with six rotating joints, a reach of 850 mm and a maximum payload of 5 kg. The arm may be controlled through the histotripsy system software as well as a 12 inch touchscreen polyscope with a graphical user interface. The robot can comprise force sensing and a tool flange, with force (x, y, z) with a range of 50 N, precision of 3.5 N and accuracy of 4.0 N, and torque (x, y, z) with a range of 10.0 Nm, precision of 0.2 Nm and accuracy of 0.3 Nm.

The robot has a pose repeatability of +/−0.03 mm and a typical TCP speed of 1 m/s (39.4 in/s). In one embodiment, the robot control box has multiple I/O ports, including 16 digital in, 16 digital out, 2 analog in, 2 analog out and 4 quadrature digital inputs, and an I/O power supply of 24V/2A. The control box communication comprises 500 Hz control frequency, Modbus TCP, PROFINET, ethernet/IP and USB 2.0 and 3.0.

The therapy head can comprise one of a select group of four histotripsy therapy transducers and an ultrasound imaging system/probe, coaxially located in the therapy transducer, with an encoded mechanism to rotate said imaging probe independent of the therapy transducer to known positions, and a handle to allow gross and fine positioning of the therapy head, including user inputs for activating the robot (e.g., for free drive positioning). In some examples, the therapy transducers may vary in size (22×17 cm to 28×17 cm), focal lengths from 12-18 cm, number of elements, ranging from 48 to 64 elements, comprised within 12-16 rings, and all with a frequency of 700 kHz. The therapy head subsystem has an interface to the robotic arm includes a quick release mechanism to allow removing and/or changing the therapy head to allow cleaning, replacement and/or selection of an alternative therapy transducer design (e.g., of different number of elements and geometry), and each therapy transducer is electronically keyed for auto-identification in the system software.

The patient coupling system can comprise a six degree of freedom, six joint, mechanical arm, configured with a mounting bracket designed to interface to a surgical/interventional table rail. The arm may have a maximum reach of approximately 850 mm and an average diameter of 50 mm. The distal end of the arm can be configured to interface with an ultrasound medium container, including a frame system and an upper and lower boot. The lower boot is configured to support either a patient contacting film, sealed to patient, or an elastic polymer membrane, both designed to contain ultrasound medium (e.g., degassed water or water mixture), either within the frame and boot and in direct contact with the patient, or within the membrane/boot construct. The lower boot provides, in one example, a top and bottom window of approximately 46 cm×56 cm and 26 cm×20 cm, respectively, for placing the therapy transducer with the ultrasound medium container and localized on the patient's abdomen. The upper boot may be configured to allow the distal end of the robot to interface to the therapy head and/or transducer, and to prevent water leakage/spillage. In preferred embodiments, the upper boot is a sealed system. The frame is also configured, in a sealed system, to allow two-way fluid communication between the ultrasound medium container and an ultrasound medium source (e.g., reservoir or fluidics management system), including, but not limited for filling and draining, as well as air venting for bubble management.

The system software and work-flow can be configured to allow users to control the system through touchscreen display and the physical controls, including but not limited to, ultrasound imaging parameters and therapy parameters. The graphical user interface of the system comprises a work-flow based flow, with the general procedure steps of 1) registering/selecting a patient, 2) planning, comprising imaging the patient (and target location/anatomy) with the freehand imaging probe, and robot assisted imaging with the transducer head for final gross and fine targeting, including contouring the target with a target and margin contour, of which are typically spherical and ellipsoidal in nature, and running a test protocol (e.g., test pulses) including a bubble cloud calibration step, and a series of predetermined locations in the volume to assess cavitation initiation threshold and other patient/target specific parameters (e.g., treatment depth), that together inform a treatment plan accounting for said target's location and acoustic pathway, and any related blockage (e.g., tissue interfaces, bone, etc.) that may require varied levels of drive amplitude to initiate and maintain histotripsy. Said parameters, as measured as a part of the test protocol, comprising calibration and multi-location test pulses, are configured in the system to provide input/feedback for updating bubble cloud location in space as needed/desired (e.g., appropriately calibrated to target cross-hairs), as well as determining/interpolating required amplitudes across all bubble cloud treatment locations in the treatment volume to ensure threshold is achieved throughout the volume. Further, said parameters, including but not limited to depth and drive voltage, may be also used as part of an embedded treatability matrix or look up table to determine if additional cooling is required (e.g., off-time in addition to time allocated to robot motions between treatment pattern movements) to ensure robust cavitation and intervening/collateral thermal effects are managed (e.g., staying below t43 curve for any known or calculated combination of sequence, pattern and pathway, and target depth/blockage). The work-flow and procedure steps associated with these facets of planning, as implemented in the system software may be automated, wherein the robot and controls system are configured to run through the test protocol and locations autonomously, or semi-autonomously. Following planning, the next phase of the procedure work-flow, 3) the treatment phase, is initiated following the user accepting the treatment plan and initiating the system for treatment. Following this command, the system is configured to deliver treatment autonomously, running the treatment protocol, until the prescribed volumetric treatment is complete. The status of the treatment (and location of the bubble cloud) is displayed in real-time, adjacent to various treatment parameters, including, but not limited to, of which may include total treatment time and remaining treatment time, drive voltage, treatment contours (target/margin) and bubble cloud/point locations, current location in treatment pattern (e.g., slice and column), imaging parameters, and other additional contextual data (e.g., optional DICOM data, force torque data from robot, etc.). Following treatment, the user may use the therapy head probe, and subsequently, the freehand ultrasound probe to review and verify treatment, as controlled/viewed through the system user interface. If additional target locations are desired, the user may plan/treat additional targets, or dock the robot to a home position on the cart if no further treatments are planned.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
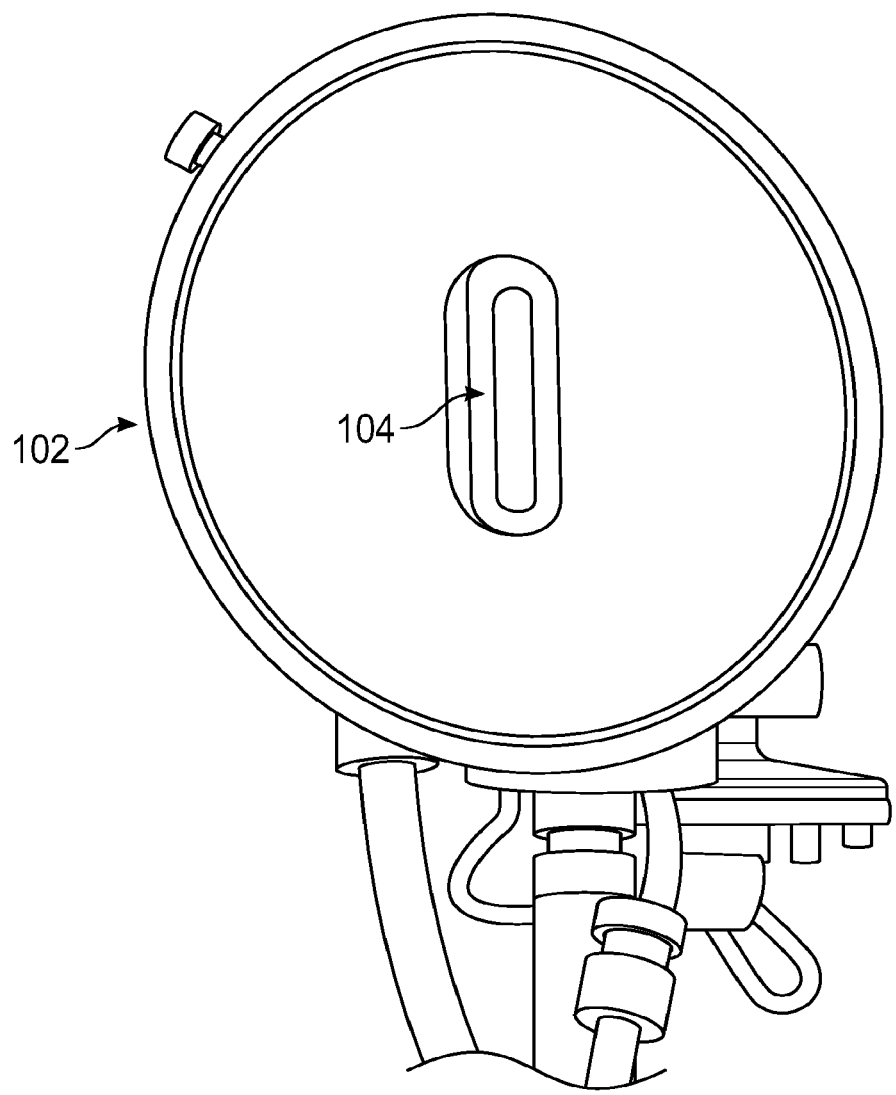

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer.

The histotripsy system may comprise one or more of various sub-systems, including a Therapy sub-system that can create, apply, focus and deliver acoustic cavitation/ histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g., compatible within cone beam CT work-space for collecting imaging data pre, peri and/or post histotripsy).

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with at least a single negative/tensile phase sufficient to cause a cluster of bubble nuclei intrinsic to the medium to undergo inertial cavitation, 2) Shock-Scattering Histotripsy: Delivers typically pulses 3-20 cycles in duration. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pin-point a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezo-electric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or auto-transformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

Figure 2:
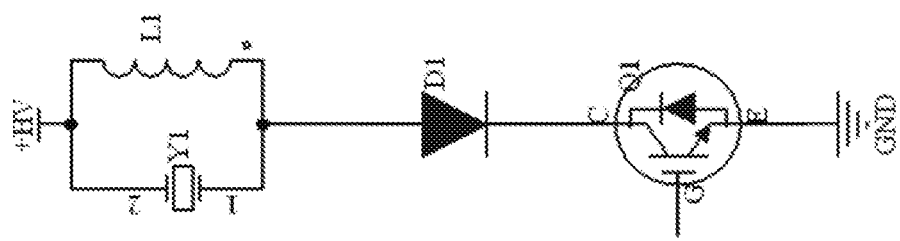
FIG. 2 provides a schematic diagram of an inductive driver circuit configured to excite ultrasound transducers for histotripsy therapy.

To sufficiently drive therapy transducers for histotripsy therapy, in other embodiments, the amplifier maybe required to produce voltages that exceed operational limits of conventional amplifier circuit components. For example, FIG. 2 provides a schematic diagram of an inductive driver circuit configured to excite ultrasound transducers for histotripsy therapy. With the inductive driver circuit of FIG. 2, therapy transducer elements can be driven up to approximately 3 kV peak-positive or up to about 4.5 kV peak-to-peak. These voltages may, for example, be adequate for a therapy transducer operating at 1 MHz but not sufficient for a 500 kHz transducer. The maximum driving voltage in this example of the inductive driver is limited by the maximum operating voltage of the IGBT transistor Q1 and its switching time. The IGBT transistor with best performance for the inductive driving circuit currently available is rated for maximum of 3 kV. It should be understood that this driving voltage can improve as advances in transistors are made.

The inductive driver circuit described above also offers many advantages to higher frequency transducers, including the ability to produce smaller/more precise bubble clouds (i.e., microtripsy), producing a reduced thermal effect in tissue, etc.

The inductive driver circuit of FIG. 2 is designed and configured to use the transducer element as a capacitor in parallel to the L1 inductor in order to create an oscillating circuit. When the IGBT transistor is excited with a single pulse, current flows through the inductor L1 which temporarily stores the energy in a magnetic field. As soon as driving pulse disappears, magnetic field is transferred back to very high amplitude electric pulse and process keeps repeating on the resonant frequency of the LC circuit (L1 and Y1 in the illustrated example). Time that is needed for inductor to be charged (aka, charging time) can vary and will proportionally affect the output amplitude. This high electric pulse is limited to 3 kV peak-positive as described above.

Although the inductive driver circuit of FIG. 2 provides higher voltages over typical Class D amplifiers, it has its own limitations, including that 1) it can be driven with only one pulse at a time. Multiple cycles are possible with increased spacing between pulses that allows for inductor charging for the next cycle; 2) in case of accidental disconnection of the transducer element, the resonant circuit will start oscillating in much higher frequency and produce amplitudes that may exceed 3 kV peak-positive which could destroy the IGBT transistor and create catastrophic failure of the system; 3) if a transducer element becomes shorted, the current will bypass the inductor and will be shorted directly to the ground through the IGBT transistor Q1, which could cause a drop in the high voltage supply or failure of the IGBT transistor due to the excessive current; and 4) the inductive driver circuit is currently limited to approximately 3 kV peak-positive or about 4.5 kV peak-to-peak.

Figure 3:
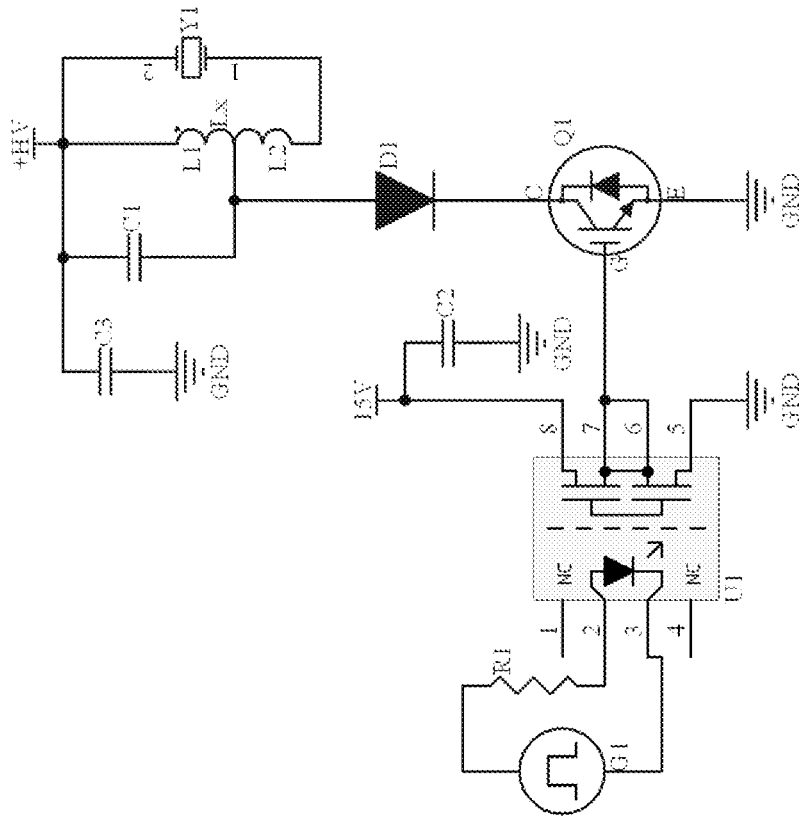
FIG. 3 illustrates a schematic diagram of an autotransforming inductive driver circuit including an inductor Lx with a center tap that solves the shortcomings of the inductive driver circuit of FIG. 2.

FIG. 3 illustrates a schematic diagram of an autotransforming inductive driver circuit including an inductor Lx with a center tap that solves the shortcomings of the inductive driver circuit of FIG. 2. In this embodiment, the driving signal is generated in the generator G1 and passes through the resistor R1 to the optically isolated IGBT driver U1. As a result, a driving square wave pulse with amplitude of 15V is generated at U1 pins 6 and 7 and applied to the gate of the IGBT transistor Q1. When signal at the gate is high (e.g., 15V), the transistor Q1 opens and current from "+HV" terminal flows through the first portion of the Lx inductor (L1), through diode D1, and through the transistor Q1 (collector to emitter) to the GND. Capacitor C3 is a bypass capacitor that supports momentarily current draw by the circuit. C3 has voltage rating that exceeds maximum "+HV" voltage and as much capacitance as necessary to support momentarily current draw. Electrical current that flows through the one part of the inductor Lx (L1) creates a magnetic field and charges the inductor Lx. As soon as driving signal goes to low, the IGBT transistor Q1 closes, and magnetic field (energy) that is created in the first part L1 of the inductor Lx is stored in the entire inductor Lx and is transformed to the electric energy across the entire inductor Lx (Lx=L1+L2).

Varying the supply voltage "+HV" in the range 0-1000V DC and varying the charging time or width of the driving pulse in the range 0-10 us, peak voltage at the center tap of the inductor Lx (where L1 is connected to L2) can reach up to 3000V peak-positive which is limited by the transistor Q1 as described earlier in the inductive driving circuit of FIG. 2. Since the inductor Lx of FIG. 3 is not just a regular inductor, but an inductor with a center tap, that makes it an autotransformer. Depending on the turn ratio between one part of the inductor Lx (L1) and the other part L2, voltage across the inductor Lx can be customized. For example: If center tap of the inductor Lx is at the center of the inductor, then the ratio between L1 to Lx will be 1 to 2 (1:2). This means that if maximum voltage generated at the L1, can be effectively doubled using autotransformer inductor as described here, and in this case, generate up to 6000V peak-positive across Lx which is applied to the therapy transducer Y1. For the therapy transducers with lower operating frequencies, higher voltage may be required in order to obtain desirable acoustic output. In that case different design of Lx with customized ratio L1:Lx is required. Using this approach (more aggressive turn ratio L1:Lx), voltages generated across Lx could be extremely high and it will be limited only by isolation limitations to safely handle the produced high voltage pulses.

As described above, the autotransformer Lx of FIG. 3 in combination with capacitor C1 and the therapy transducer Y1 creates a resonant circuit configured to be used as a pulse generator able to generate very high voltage AC pulses for driving a therapy transducer, which produces maximum acoustic output needed for Histotripsy therapy.

The total value of the inductor Lx of FIG. 3 can be determined based on the electric impedance and operating frequency of the transducer element. In some examples, the value of the inductor Lx can be determined based on the optimally desired acoustical output (desired frequency of the pulses, peak positive and peak negative pressures per voltage in, etc. . . . ). For Histotripsy, the application total value of the inductor Lx could be in range of 1-1000 uH.

As described above, the center frequency of the therapy transducer is proportional to the thickness of the piezoelectric material that the therapy transducer is made of. Therefore, the thickness of the piezoelectric will determine maximum safe operating voltage needed in order to output maximum acoustic pressure. Additionally, the maximum operating voltage will determine the inductor (autotransformer) turn ratio (L1:Lx) needed. In other words, it will determine where on the inductor winding a center tap needs to be placed which when placed turns the inductor into the autotransformer.

Capacitor C1 in the circuit of FIG. 3 is a very important part of the circuit. Connected together in parallel with part of the autotransformer L1, the capacitor C1 creates a resonant circuit that oscillates in same frequency as the autotransformer Lx in parallel with the therapy transducer Y1. The voltage rating of the capacitor C1 should be at least 10% higher than the maximum driving voltage. The capacitance value of the capacitor C1 is determined using the following formula for calculating resonant frequency:

$$f_0 = \frac{\omega_0}{2\pi} = \frac{1}{2\pi\sqrt{LC}}$$

However, a slight change of the capacitor value can fine tune the resonant frequency of the entire circuit. It is recommended that final value of the capacitor be determined by desired acoustical output (peak-positive pressure, peak-negative pressure, frequency, etc. . . . ). For Histotripsy therapy, for example, the value of the capacitor C1 could be in range of 100 pF-100 nF.

Figure 4:
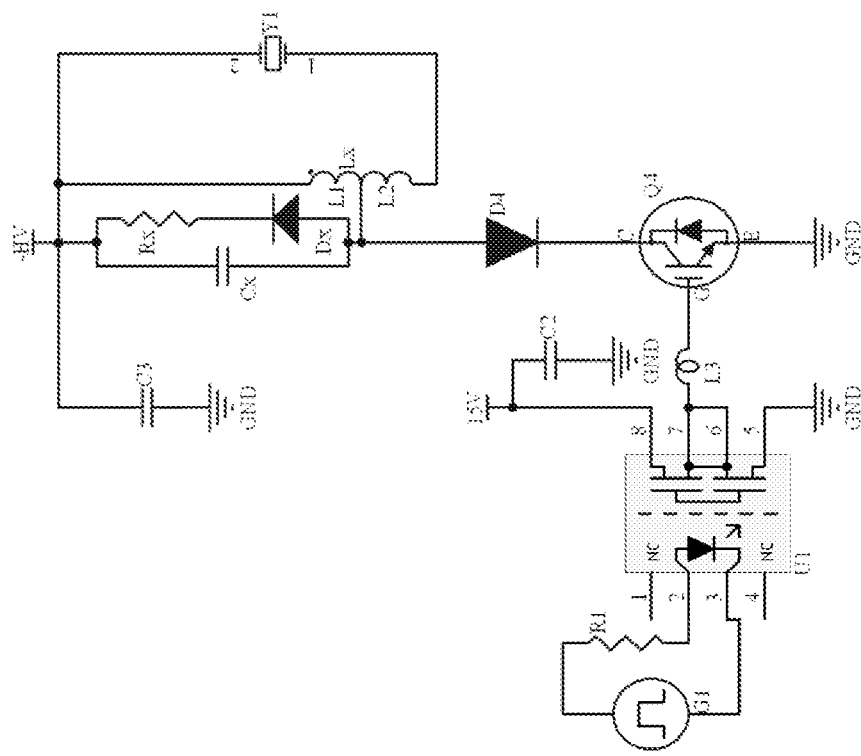
FIG. 4 illustrates a schematic diagram of an autotransforming inductive driver with another active or passive electronic component.

The capacitor C1 of FIG. 3 can be substituted with another active or passive electronic component such as a resistor, diode, inductor, etc. as well as a combination of multiple different components. For example: if a capacitor C1 is substituted with the combination of components like capacitor Cx, diode Dx, and resistor Rx in a manner shown in FIG. 4, it is possible to obtain even more asymmetric waveform with larger negative peak or larger positive peak depending on the orientation of the diode Dx. The level of asymmetry is determined by the value of the resistor Rx and the frequency by the value of the capacitor Cx. The switching transistor Q4 can be an IGBT transistor, or any other high-power switching devices like MOSFET, Bipolar Transistors, or others.

The autotransforming inductive driver circuit of FIG. 3 provides the ability to create very high amplitudes without the limitations of class D and the inductive driver generators described above. As mentioned, in case of a single fault condition where the therapy transducer gets disconnected, very high voltage peaks that can destroy the IGBT transistor Q1 will not be generated by the autotransforming inductive driver circuit and therefore the catastrophic failure of the system will not occur. In event of this situation, the IGBT transistor Q1 continues to operate in normal conditions because of the resonant circuit comprised of the capacitor C1 and the inductor L1 (primary portion of the autotransformer Lx) are still operating normally as they were if the therapy transducer Y1 is connected.

In case of a single fault condition where the therapy transducer gets shorted, extensive current flow that can destroy the IGBT transistor Q1, or shorting of the high voltage power Supply "+HV" will not occur and therefore the catastrophic failure of the system will not occur as it would with a regular inductive driver generator. The IGBT transistor Q1 continues to operate in normal conditions because of the resonant circuit comprised of the capacitor C1 and the inductor L1 (primary portion of the autotransformer Lx) are still operating normally as they were if the therapy transducer Y1 is connected.

Alternatively, for additional safety for the service personnel and users in general, the auto transforming inductive driver circuit of FIG. 3 can be supplied with the negative voltage supply. In that case +HV terminals as shown in the figures described above can be connected to the ground (GND) and ground terminals can be connected to the negative voltage supply (-HV) as shown in the FIG. 5. Note that the 15V power supply is in reference to the -HV terminal. This is easily obtained using isolated DC/DC converter where the negative secondary terminal is connected to the -HV terminal. That isolated DC/DC converter has to be properly rated for the level of -HV power supply.

The main safety benefit of the negative voltage supply is that one of the electrodes (typically shielding of the BNC or another connector) of the transducer is always connected to the ground (GND) and therefore safe for the operator or service person to touch, connect or disconnect the transducer while the amplifier is energized. If the circuit is supplied conventionally with positive supply voltage, one electrode of the transducer will be connected to the high voltage power supply and therefore not safe to be handled.

Figure 5:
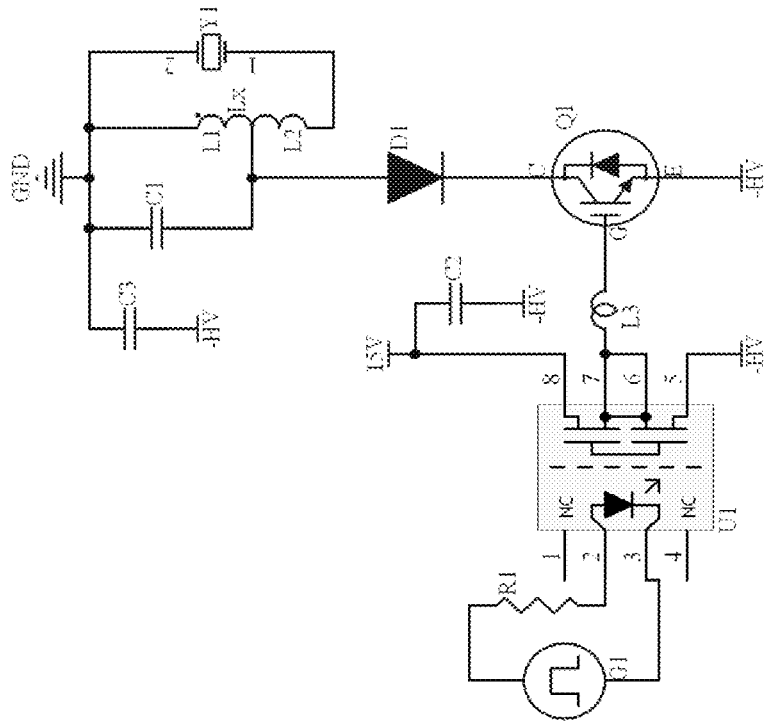
FIG. 5 illustrates a schematic diagram of an autotransforming inductive driver with a protective circuit.
Figure 6:
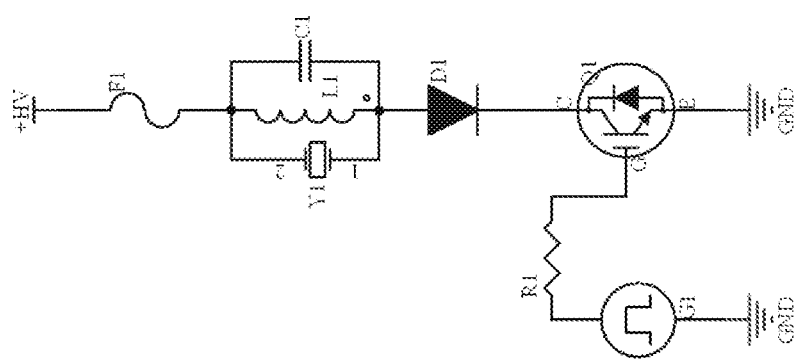
FIG. 6 illustrates another schematic diagram of an autotransforming inductive driver with a protective circuit.

It is also possible to apply the protective circuit of FIG. 5 by adding the capacitor C1 in parallel to the inductor L1 and the ultrasonic transducer Y1 shown in FIG. 6. The value of the capacitor C1 can be calculated to be as minimal as needed to have the oscillating circuit oscillate within safe frequency and voltage angle ranges to prevent generation of voltages that exceed the working voltage of the transistor Q1 in the event that the ultrasonic transducer gets disconnected or fails with an open circuit.

The combined capacitance of the capacitor C1 and the transducer Y1 is used to calculate the working frequency of the resonant circuit (i.e., capacitor C1, inductor L1, and ultrasonic transducer Y1). Alternatively, changing the value of the capacitor C1 can be used to fine-tune the operating frequency of the entire circuit.

In the event of the short circuit failure mode of the transducer, the fast-acting fuse is connected in series to the power source +HV. The value of the fast-acting fuse F1 is calculated to be a 10% or higher than the current consumption of the entire circuit at the maximum amplitude and duty cycle. If a failure occurs, direct current will start flowing through the shorted transducer Y1 and the transistor Q1. At that time, the fast-acting fuse F1 will open due to the excessive current which will protect the transistor Q1 and the entire system from catastrophic failure.

The Therapy sub-system may also comprise therapy transducers of various designs and working parameters, supporting use in various procedures (and procedure settings). Systems may be configured with one or more therapy transducers, that may be further interchangeable, and work with various aspects of the system in similar or different ways (e.g., may interface to a robotic arm using a common interface and exchange feature, or conversely, may adapt to work differently with application specific imaging probes, where different imaging probes may interface and integrate with a therapy transducer in specifically different ways).

Therapy transducers may be configured of various parameters that may include size, shape (e.g., rectangular or round; anatomically curved housings, etc.), geometry, focal length, number of elements, size of elements, distribution of elements (e.g., number of rings, size of rings for annular patterned transducers), frequency, enabling electronic beam steering, etc. Transducers may be composed of various materials (e.g., piezoelectric, silicon, etc.), form factors and types (e.g., machined elements, chip-based, etc.) and/or by various methods of fabrication of.

Transducers may be designed and optimized for clinical applications (e.g., abdominal tumors, peripheral vascular disease, fat ablation, etc.) and desired outcomes (e.g., acoustic cavitation/histotripsy without thermal injury to intervening tissue), and affording a breadth of working ranges, including relatively shallow and superficial targets (e.g., thyroid or breast nodules), versus, deeper or harder to reach targets, such as central liver or brain tumors. They may be configured to enable acoustic cavitation/histotripsy under various parameters and sets of, as enabled by the aforementioned system components (e.g., function generator and amplifier, etc.), including but not limited to frequency, pulse repetition rate, pulses, number of pulses, pulse length, pulse period, delays, repetitions, sync delays, sync period, sync pulses, sync pulse delays, various loop sets, others, and permutations of.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into the system's Therapy sub-system components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging component or probe may be encoded so its orientation and position relative to another aspect of the system, such as the therapy transducer, and/or robotically-enabled positioning component may be determined.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastography); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treatment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image(s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci* Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Robotics

They system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others.

In some cases, sensors may be used for users to direct robot commands (e.g., hand gesture the robot into a preferred set up position, or to dock home). Additional details on robotic arms can be found in US Patent Pub. No. 2013/0255426 to Kassow et al., which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Coupling

Systems may comprise a variety of Coupling sub-system embodiments, of which are enabled and configured to allow acoustic coupling to the patient to afford effective acoustic cavitation/histotripsy (e.g., provide acoustic medium between transducer and patient, and support of). These may include different form factors of such, including open and enclosed solutions, and some arrangements which may be configured to allow dynamic control over the acoustic medium (e.g., temperature, dissolved gas content, level of particulate filtration, sterility, etc.). Such dynamic control components may be directly integrated to the system (within the Cart), or may be in communication with the system, but externally situated.

The Coupling sub-system typically comprises, at a minimum, coupling medium, a reservoir/container to contain said coupling medium, and a support structure. In most embodiments, the coupling medium is water, and wherein the water may be conditioned before or during the procedure (e.g., chilled, degassed, filtered, etc.). Various conditioning parameters may be employed based on the configuration of the system and its intended use/application.

The reservoir or medium container may be formed and shaped to adapt/conform to the patient, allow the therapy transducer to engage and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. The container may be of various shapes, sizes, curvatures, and dimensions, and may be comprised of a variety of materials (single, multiple, composites, etc.), of which may vary throughout. In some embodiments, it may comprise features such as films, drapes, membranes, bellows, etc. that may be insertable and removable, and/or fabricated within. It may further contain various sensors, drains, lighting (e.g., LEDs), markings, text, etc.

In one embodiment, the reservoir or medium container contains a sealable frame, of which a membrane and/or film may be positioned within, to afford a conformable means of contacting the reservoir (later comprising the therapy transducer) as an interface to the patient, that further provides a barrier to the medium (e.g., water) between the patient and transducer). In other embodiments, the membrane and/or film may comprise an opening, the edge of which affords mechanical sealing to the patient, but in contrast allows medium communication with the patient (e.g., direct water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoplastic elastomers, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability. In some embodiments, the thermoplastic elastomer may be styrene-ethylene-butylene-styrene (SEBS), or other like strong and flexible elastomers.

Said materials may be formed into useful membranes through molding, casting, spraying, ultrasonic spraying and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc. Membranes can be further configured with an outer molded frame to provide mechanical stability during assembly of the coupling sub-system. Various parameters of the membrane can be optimized for this method of use, including thickness, thickness profile, density, formulation (e.g., polymer molecular weight and copolymer ratios), including optimizing specifically to maximize acoustic properties, including minimizing impact to cavitation initiation threshold values, and/or ultrasound imaging artifacts, including but not limited to membrane reflections.

Open reservoirs or medium containers may comprise various methods of filling, including using pre-prepared medium or water, that may be delivered into the such, in some cases to a defined specification of water (level of temperature and gas saturation, etc.), or they may comprise additional features integral to the design that allow filling and draining (e.g., ports, valves, hoses, tubing, fittings, bags, pumps, etc.).

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing and control systems, etc.

Coupling support systems may include various mechanical support devices to interface the reservoir/container and medium to the patient, and the workspace (e.g., bed). In some embodiments, the support system comprises a mechanical arm with 3 or more degrees of freedom. Said arm may interface with one or more locations (and features) of the bed, including but not limited to, the frame, rails, customized rails or inserts, as well as one or more locations of the reservoir or container. The arm may be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.).

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and maybe used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Other Components, Ancillaries and Accessories

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use "apps" or user training materials and applications (software or paper based), virtual proctors or trainers and/or other enabling features, devices, systems or applications, and/or methods of using the above.

System Variations and Methods/Applications

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the test protocols and optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and "universal" amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, immuno-oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular and/or neuro-related spaces, cosmetics/aesthetics, metabolic (e.g., type 2 diabetes), plastics and reconstructive, ocular and ophthalmology, gynecology and men's health, and other systems, devices and methods of treating diseased, injured, undesired, or healthy tissues, organs or cells.

Treatment Patterns

Systems and methods are also provided for improving treatment patterns within tissue that can reduce treatment time, improve efficacy, and reduce the amount of energy and prefocal tissue heating delivered to patients. In some embodiments, the treatment patterns describe the way in which the bubble cloud is moved or manipulated within a target tissue volume to ablate the tissue volume.

A "Standard Z" (SZ) pattern is the treatment path that traverses the spherical volume in a series of axial slices (parallel to the imaging plane), beginning with the center slice and progressing outward in the positive x-dimension until the entire +x-half of the sphere is treated. The treatment then moves to the untreated slice adjacent to the center and treats the remaining half of the spherical volume in an analogous manner, in this case progressing outward in the negative x-dimension. Within each slice, treatment starts at the center point and moves outward in a spiraling fashion.

The "Top-Down" and "Bottom-Up" patterns differ from the SZ pattern in that they do not traverse the volume in axial slices; rather, they progress through the sphere in a series of lateral slices (i.e., slices perpendicular to the acoustic axis of the therapy transducer). Within each slice, treatment starts at the center point and moves outward in a spiraling fashion (identical to the manner in which the SZ pattern traverses an axial slice). As the names imply, the "Top-Down" and "Bottom-Up" patterns progress through the lateral planes of the sphere from the upper-most (closest to the transducer) to the distal-most (farthest from the transducer) or distal-most to upper-most, respectively.

Figure 7B:
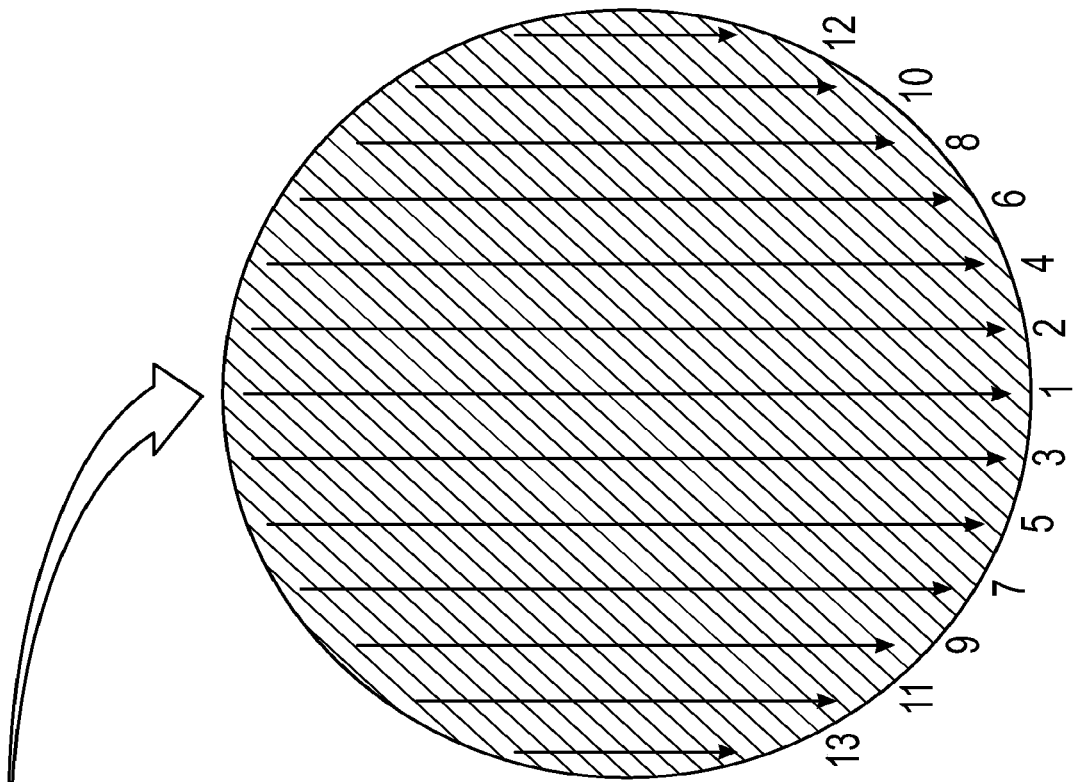
FIGS. 7A and 7B illustrate one example of a treatment pattern for ablating a target tissue volume.
Figure 7A:
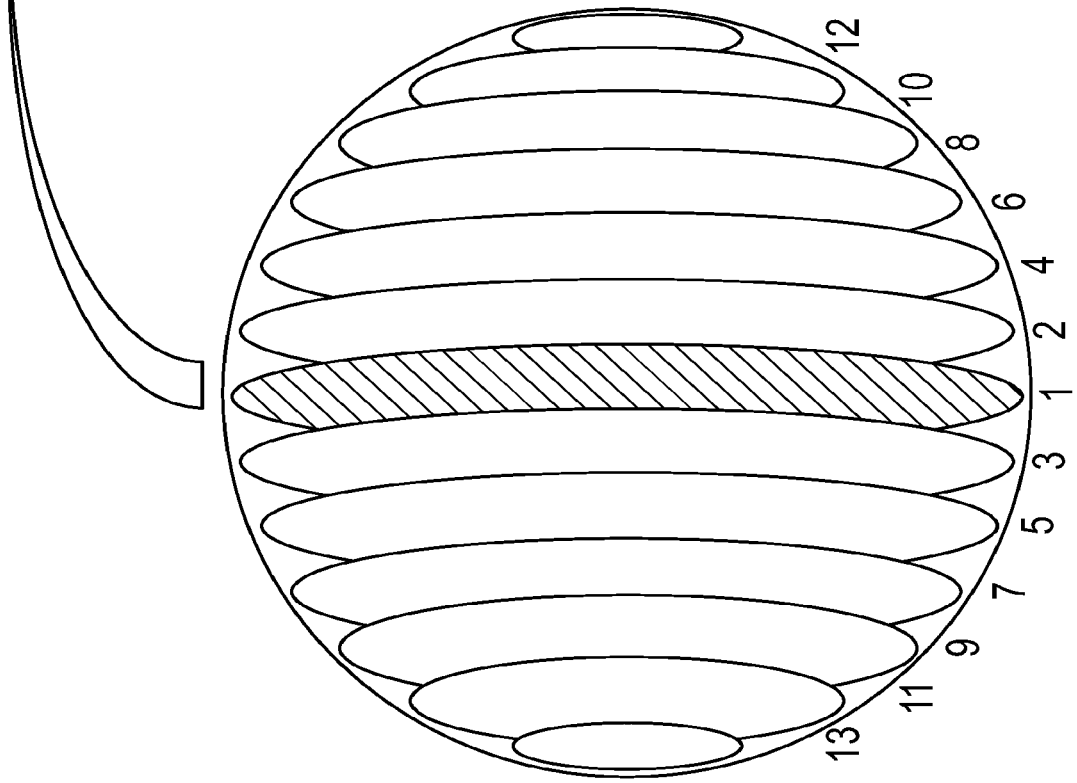

FIGS. 7A-7B provide illustrations of a "DZ" pattern. The target tissue volume is divided into a number of slices (e.g., 13 slices in the example shown in FIG. 7A), which are treated in alternating order starting from the middle of the volume (number below each slice indicates treatment order). Within each slice, as shown in FIG. 7B, columns are treated in an alternating fashion (number below each column indicates treatment order). The columns themselves can be traversed in a top-down or a bottom-up manner, depending on the treatment type, tissue, type, and tissue location.

The "Standard Z Side-Side" and "Standard Z Shuffle" patterns represent variations of the SZ pattern. The spherical volume is still traversed in a set of axial slices parallel to the imaging plane, and the progression of treatment within each slice remains the same. Only the order in which the axial slices are treated is varied in these two schemes. Specifically, the "Standard Z Side-Side" pattern treats the axial slices starting at one lateral extreme of the volume (e.g., the slice farthest in the +x-dimension) and progresses through slices one at a time until reaching the other lateral extreme of the volume (the slice farthest in the −x-dimension). The "Standard Z Shuffle" pattern increments through slices in a strategic order selected to maximize the spatial distribution of successive treatment slices. If the center axial slice of the sphere is defined as slice 0, the slice farthest in the +x-dimension as 6, and the slice farthest in the −x-dimension as −6, then the "Standard Z Shuffle" progresses through the 13 slices comprising the 3 cm sphere in the following order: 0, 4, −2, −5, −1, 6, −3, 5, 1, −6, 3, −4, 2.

The "Spiral In-Out" pattern traverses the spherical volume in a series of radial layers, from the center of the sphere outward. Within each layer, and when transitioning between layers, the points are treated in order of proximity (i.e., the next treatment point is the closest untreated point in the current radial layer, or the closest point in the next radial layer when transitioning between layers).

Figure 9:
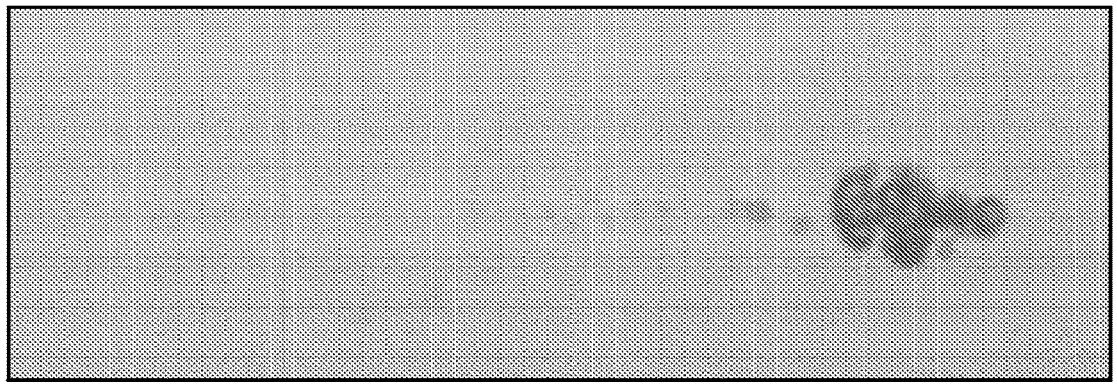
FIGS. 8-9 illustrate examples of a column shaped bubble cloud.
Figure 8:
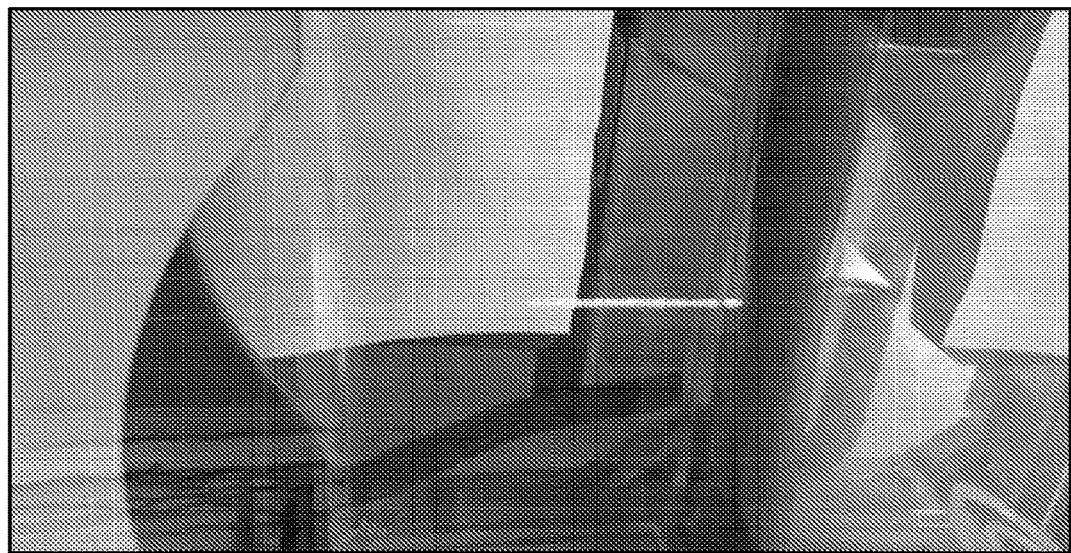

In one example, histotripsy therapy can be applied in a "bubble saber" or column shape. The "bubble saber" or column shape can be implemented by rapidly electronically steering the bubble cloud focus in the z-direction through a column of treatment points, and repeating the column treatment multiple times, thereby removing the need to mechanically move the bubble cloud in the z-direction. The "bubble saber" technique can provide a large thermal benefit to by electronically steering the bubble cloud to a more proximal location than the geometric focus to ablate shallower targets. The primary thermal benefit of the "bubble saber" technique comes from the electronic steering itself (utilization of the lowest possible effective f number). Another benefit of the "bubble saber" is the reduced impact of motion on local dose, and the potential efficacy benefits of a more parallel treatment strategy (some protection against intact "chunks" of tissue moving to a previously treated area and escaping further treatment). FIGS. 8-9 illustrate examples of a column shaped bubble cloud, illuminated by a laser in FIG. 8 and shown under real-time ultrasound imaging in FIG. 9 (an optical image is shown in FIG. 9, but it should be understood that real-time imaging such as ultrasound can also be used).

Figure 10:
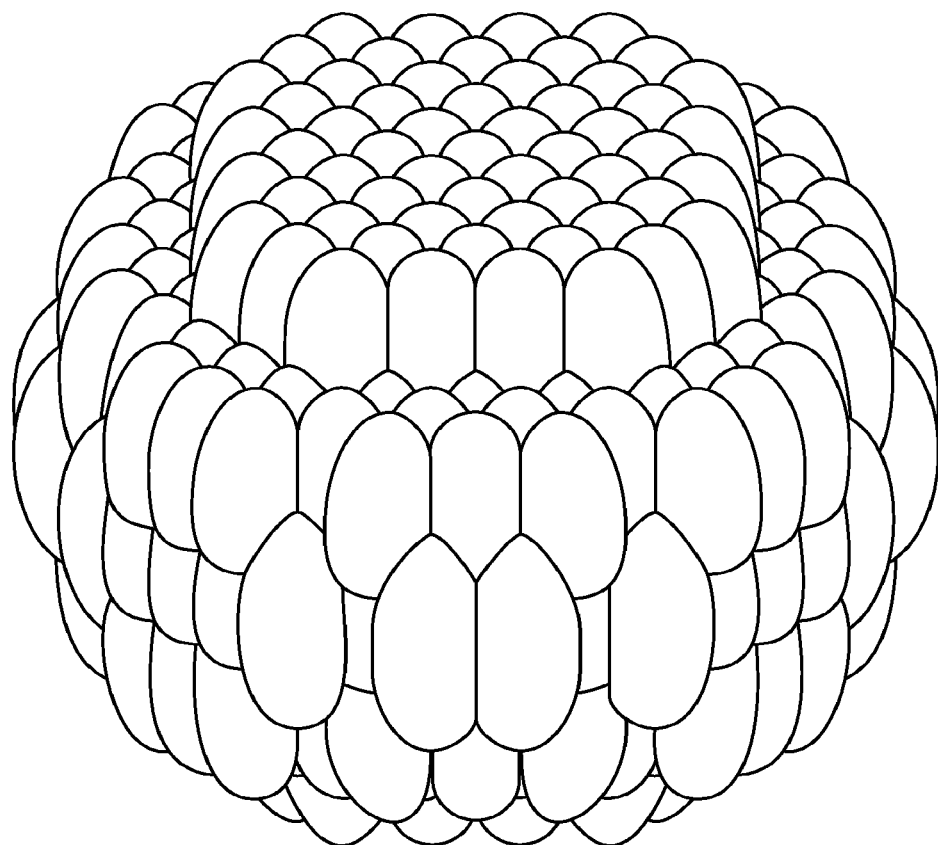
FIG. 10 illustrates an example of a rectilinear treatment pattern.
Figure 11A:
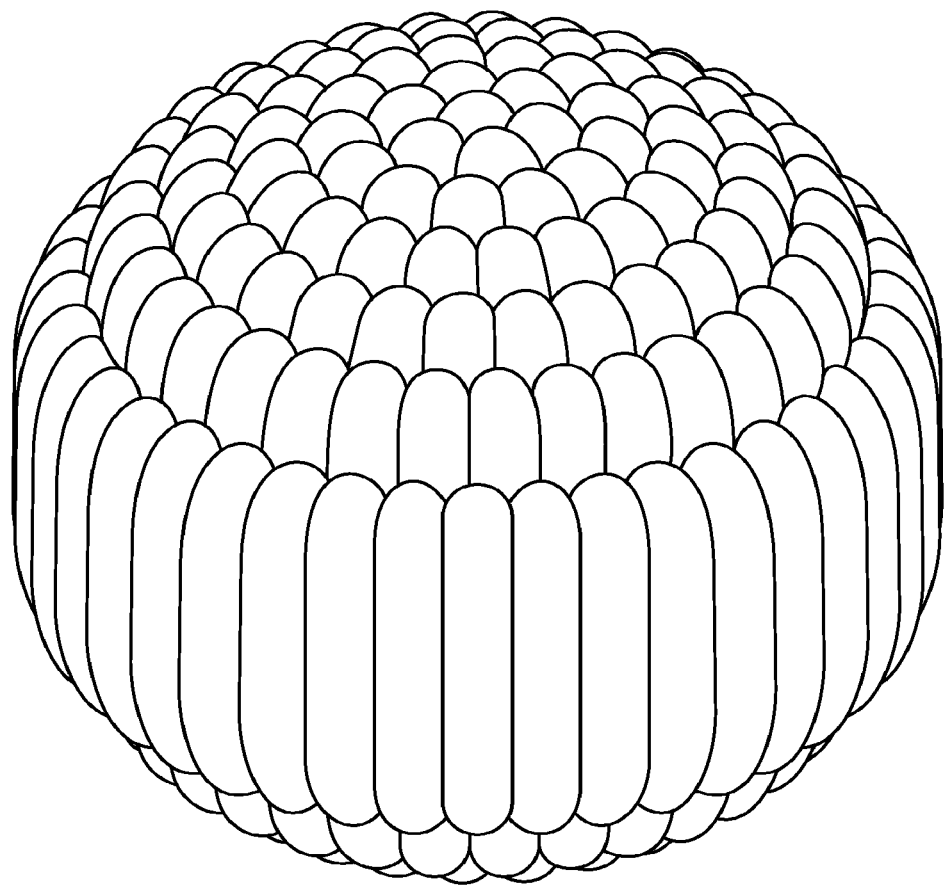
FIGS. 11A, 11B, 11C, 11D and 11E illustrate examples of a radial treatment pattern.

In another embodiment, histotripsy therapy can be applied in a "radial spiral" pattern that minimizes the distance between treatment columns while maintaining an "inside-out" lesion development in tissue. Instead of columns of treatment points arranged in a cartesian grid of locations, the treatment points in this technique are arranged in radial layers. These layers are then treated from inside out, with columns within each layer treated sequentially around each ring in a spiral (or alternating from side to side if preserving the thermal benefit of sequential treatment columns being are distant as possible is required). This pattern, illustrated in FIG. 11A, provides a more consistent cloud overlap in three-dimensions and minimized the distance between successive treatment columns compared to a rectilinear treatment pattern (as illustrated in FIG. 10), resulting in a planned ablation volume that more closely matches ellipsoidal planning contours.

The radial spiral technique allows the flexibility to reduce treatment times by removing the de facto cooling time when moving between spatially distant treatment columns. It is important to note though that this pattern does not remove the need for this cooling time, it only allows the flexibility to include or exclude cooling time only as required by the anticipated thermal load, i.e., the option to go faster if thermally tolerable.

Figure 11C:
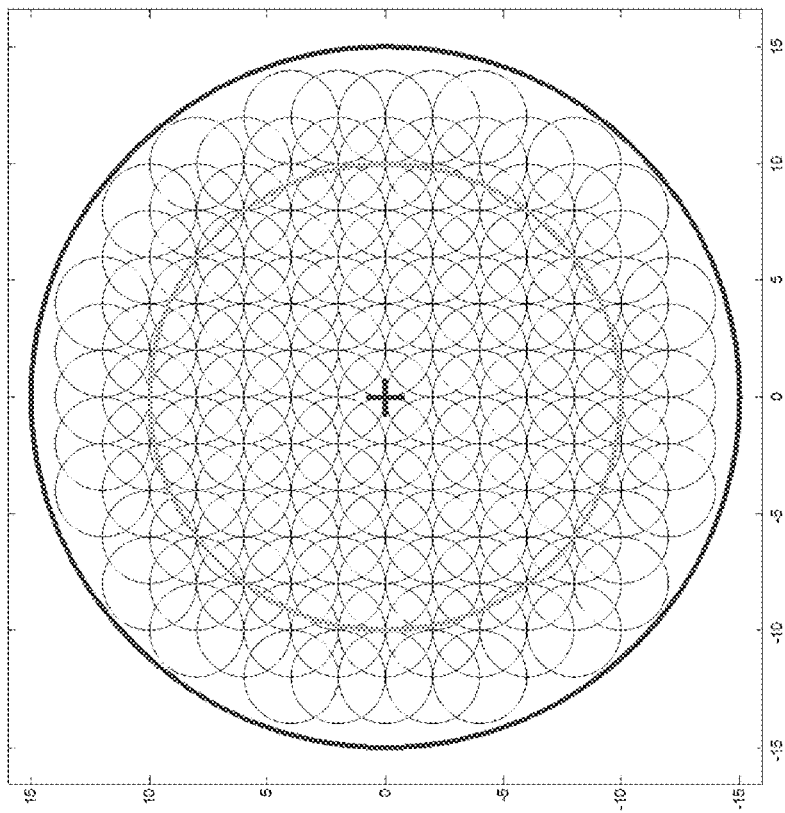
Figure 11B:
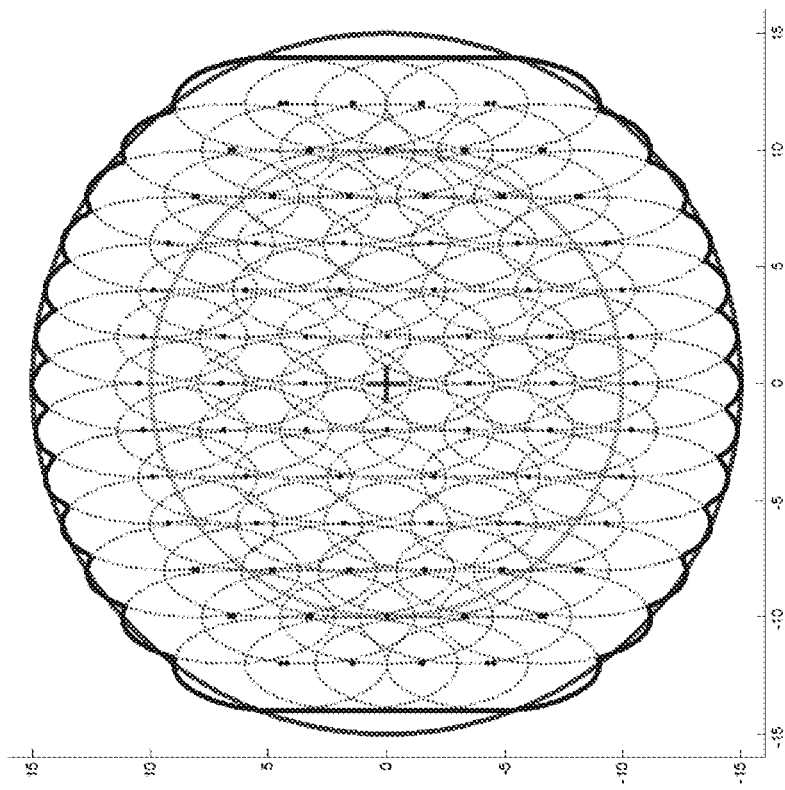

FIGS. 11B and 11C illustrate additional side and top views of a radial spiral pattern, showing how each of the individual planned bubble cloud treatments fills the target tissue volume. It can be seen from these images that the radial spiral pattern covers nearly the entire tissue volume. In some embodiments, the radial spiral pattern can be implemented to cover 90-100% of the target tissue volume. Ablation center points for each bubble cloud are distributed at discrete spacing in X and Y, with any points outside the tissue volume boundary discarded. Point positions in Z are dynamically adjusted to match the tissue volume boundary contour.

Figure 11E:
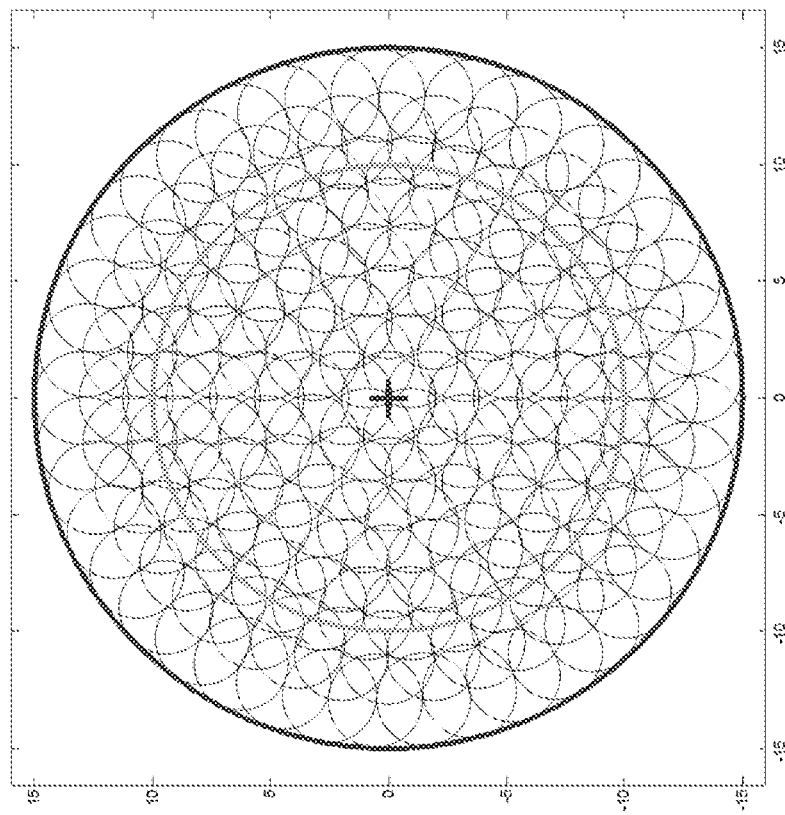
Figure 11D:
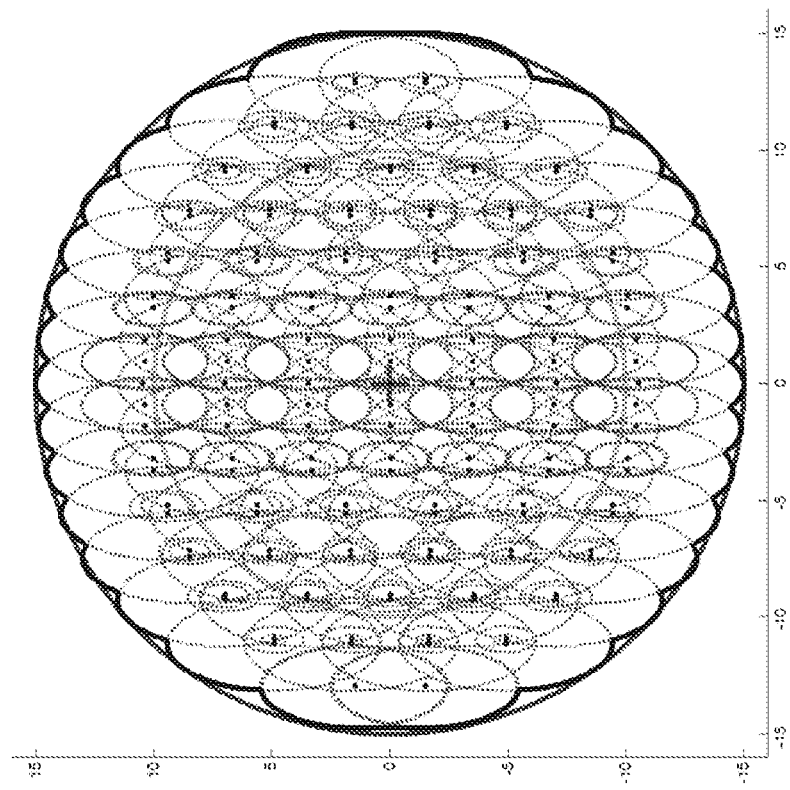

FIGS. 11D-11E show another implementation of a radial spiral pattern. In this example, ablation center points for each bubble cloud are distributed in radial layers in X and Y, with radii dynamically adjusted to match the target tissue volume boundaries. Point positions in Z are also dynamically adjusted to match the target tissue volume boundary contours. Column treatment strategy is preserved, with no significant gaps between treatment ellipsoids and the target tissue volume contours in any dimension. In some embodiments, this radial spiral pattern can be implemented to cover 95-100% of the target tissue volume.

Threshold Testing

Figure 12:
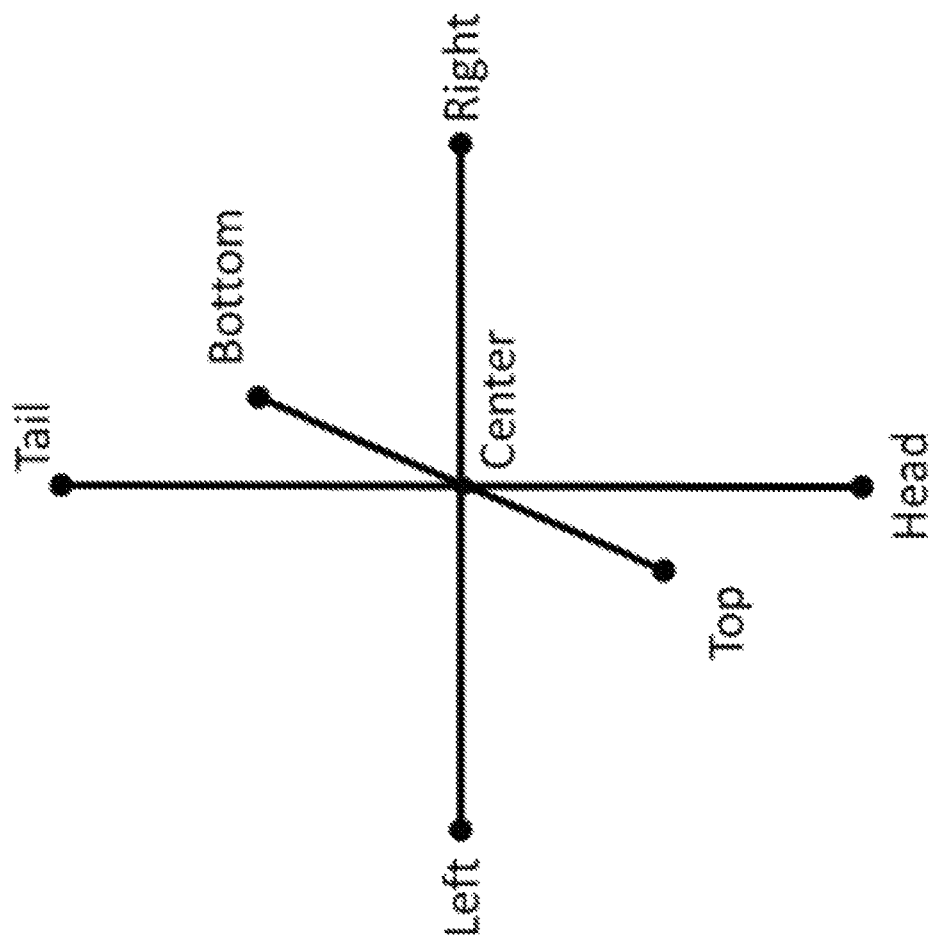
FIG. 12 is an illustration of one example of using seven test pulse locations within a spherical treatment volume.

As described above, the systems described herein include the capability to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. During treatment planning or during therapy, cavitation threshold test pulses can be transmitted into a plurality of locations of interest. The number of test locations of interest can be chosen based on the size and/or shape of the treatment region. For example, a spherical treatment region benefits from at least seven test locations to probe the extremes of the spherical volume. FIG. 12 is an illustration of one example of using seven test pulse locations within a spherical treatment volume. In this illustrated example, the test protocol and test pulses can be positioned at 1) the center of the treatment volume, 2) the proximal-most aspect of the treatment volume (top), 3) the distal-most aspect of the treatment volume, 4) the left-most aspect of the treatment volume, 5) the right-most aspect of the treatment volume, 6) the cranial-most aspect of the treatment volume (head), and 7) the caudal-most aspect of the treatment volume (tail).

During therapy, the cavitation threshold at each of the locations of interest can be evaluated with a single therapy PRF to determine if cavitation has formed before incrementing to the next PRF. For example, the formation (or not) of cavitation can be observed in real-time with imaging such as ultrasound imaging. In general, the driving voltage required to initiate a vigorous bubble cloud in tissue decreases as the therapy PRF increases. The cavitation threshold in the tissue can also vary as a treatment procedure progresses. Thus, testing various points of interest within a treatment volume during treatment can be a useful tool to evaluate the cavitation threshold(s) in real-time and adjust the PRF and/or driving voltage of the therapy pulses to optimize treatment at each of the tested locations. The treatment protocol itself can then be adjusted based on the test pulses to utilize variable amplitudes/PRF based on the test results to ensure the optimal amount of energy is delivered into each location of the tissue for histotripsy therapy. Additionally, the depth at each of the test locations can be measured or determined (either manually or automatically with the system) to provide additional information to the system for determining optimal treatment parameters.

In some embodiments, the test locations can be used to determine a maximum amount of energy that may be applied without generating undesired damage to the test location or surround or intervening tissues. For example, while determining the cavitation thresholds at each of the test locations, the drive voltage and/or PRF of the system can be increased until cavitation is observed under real-time imaging. In some embodiments, the drive voltage and/or PRF can be increased until undesirable damage to the test location or cavitation/thermal damage to other locations outside of the test location are observed. This can be used to determine the maximum amount of energy that can be applied for a given test location.

Based on the test protocol and tested cavitation thresholds, the appropriate driving voltage for each point in the treatment grid can be chosen. With the required voltage at the center and six extremes of the target volume serving as inputs, the voltages for the remaining points comprising the treatment volume can be interpolated. The driving voltage can then be adjusted automatically by the software as the therapy progresses through the automated treatment volume. In this way each point is ablated using an amplitude sufficient to maintain an efficacious bubble cloud, but not overly so in order to minimize the thermal deposition in the acoustic path.

For example, a method of delivering histotripsy therapy to tissue can comprise delivering histotripsy pulses into tissue at a plurality of target test locations and imaging the test location in real-time to evaluate whether cavitation has formed at the test locations. If cavitation has not formed at the test locations, the driving voltage and/or the PRF of the histotripsy pulses can be adjusted, and histotripsy pulses with the adjusted parameters can be delivered into the tissue at the test locations. Real-time imaging can again be used to evaluate whether cavitation has formed at each test location. This process can be repeated until the cavitation threshold at each test location is determined, and a high-density map can be created based on various algorithms to extrapolate thresholds across the targeted region of interest/treatment volume, specific to the acoustic pathway and target depth. For example, if cavitation thresholds are known at a first test location and a second test location, then the cavitation threshold at a third test location can be extrapolated based on the cavitation thresholds of the first and second test locations. This extrapolation can be further based on the tissue type, target tissue depth, and acoustic pathway of the third test location.

In one example, a method of treating tissue can comprise transmitting ultrasound pulses into a first test location with at least one ultrasound transducer, determining a first cavitation threshold at the first test location, transmitting ultrasound pulses into a second test location with the at least one ultrasound transducer, determining a second cavitation threshold at the second test location, adjusting a first driving voltage and/or PRF of the at least one transducer based on the first cavitation threshold, transmitting ultrasound pulses into the first test location with the at least one ultrasound transducer at the first adjusted driving voltage and/or PRF to generate cavitation at the first test location, adjusting a second driving voltage and/or PRF of the at least one transducer based on the second cavitation threshold, and transmitting ultrasound pulses into the second test location with the at least one ultrasound transducer at the second adjusted driving voltage and/or PRF to generate cavitation at the second test location.

Treatment Pulse Sequences and Thermal Management

A given Histotripsy therapy or treatment session can be defined in terms of a set number of pulses N that are to be delivered over a set total treatment time T. The number of pulses delivered every second by the systems described herein is defined by the pulse repetition frequency (PRF) of the system, which can be adjusted during therapy depending on the cavitation threshold, the tissue type, depth, etc. Thus, the total number of pulses N delivered over the total treatment time T (in seconds) is equal to the total treatment time T multiplied by the PRF of the system. For example, a system operating at a constant 200 Hz PRF for a total treatment time of 10 minutes (600 seconds) will have a total number of pulses N equal to 120,000. The systems and methods described herein can include PRF's of 400 Hz or greater to generate acoustic cavitation, including PRF's ranging from 400 to 900 Hz.

Systems and methods are provided herein that implement Histotripsy pulse sequences with frequent short cooling periods that advantageously improve the thermal profile generated by histotripsy treatment, with the limiting case of N pulses equally distributed over the treatment time T yielding the minimum temperature rise. These pulse sequences can further be characterized in terms of the amount of time in which therapy is actively delivered to tissue relative to the amount of cooling time in which no therapy pulses are delivered to tissue. For example, a system delivering therapy pulses at a 400 Hz PRF for 5 minutes, followed by a 5 minute cooling time in which no therapy pulses are delivered (for a total treatment time of 10 minutes) would have a ratio of therapy (5 minutes) to cooling (5 minutes) of 1:1.

Figures 13A, 13B:
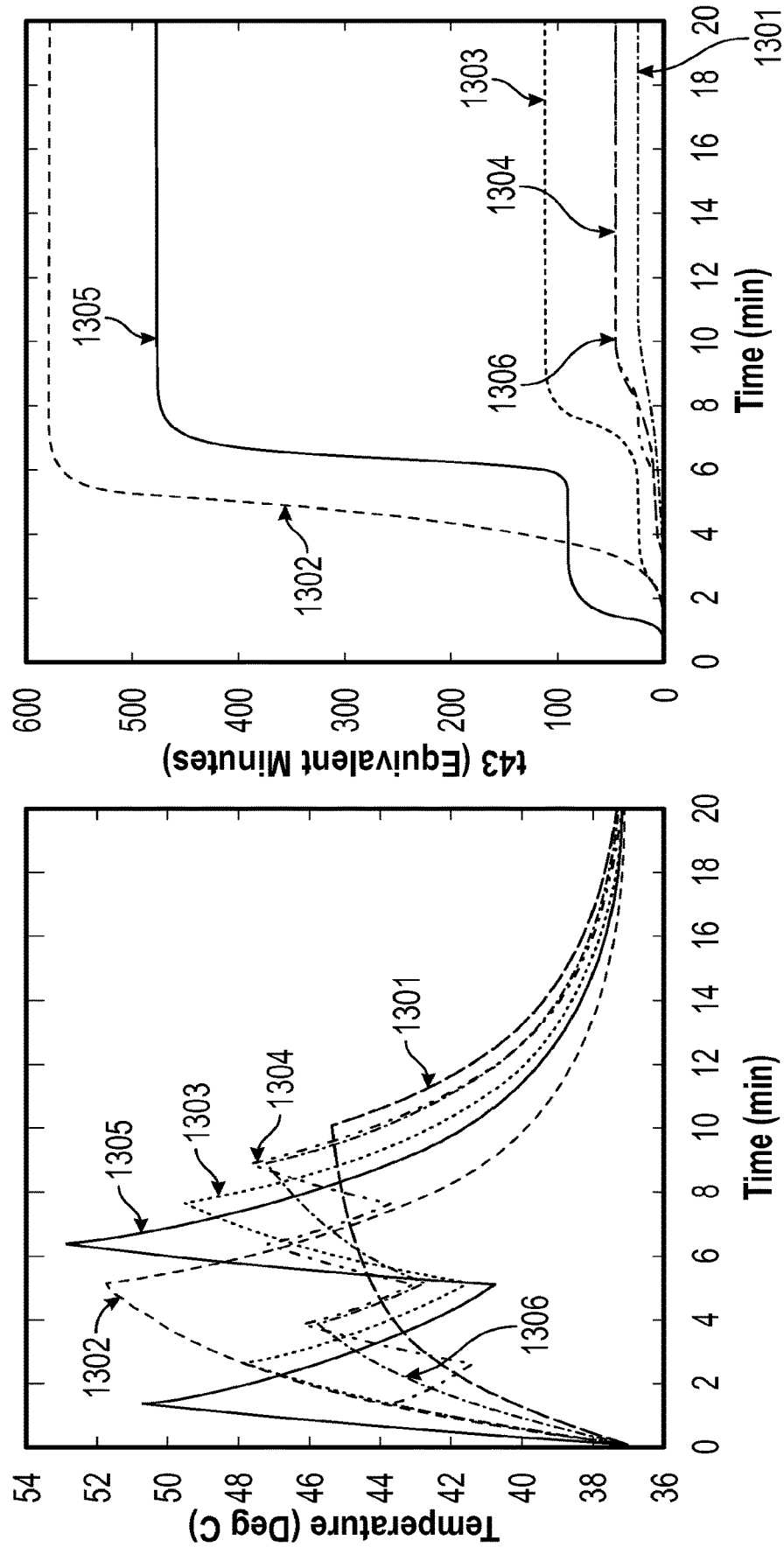
FIGS. 13A-13B illustrate temperature profiles resulting from six different histotripsy pulse schemes.

FIG. 13A illustrates temperature profiles resulting from six pulse schemes, while the corresponding t43 curves are shown in FIG. 13B. The pulse schemes illustrated comprise the following over a total treatment time of 10 minutes:

Scheme 1301: 200 Hz PRF for 10 minutes.

Scheme 1302: 400 Hz PRF for 5 minutes, followed by a 5 minute cooling time

Scheme 1303: 400 Hz PRF for 2.5 minutes, followed by 2.5 minutes of cooling with therapy and cooling repeated until total treatment time of 10 minutes is achieved.

Scheme 1304: 400 Hz PRF for 1.25 minutes, followed by 1.25 minutes of cooling with therapy and cooling repeated until total treatment time of 10 minutes is achieved.

Scheme 1305: 800 Hz for 1.25 minutes, followed by 3.75 minutes of cooling with therapy and cooling repeated until total treatment time of 10 minutes is achieved.

Scheme 1306: 266.67 Hz for 3.75 minutes, followed by 1.25 minutes of cooling with therapy and cooling repeated until total treatment time of 10 minutes is achieved.

As shown in FIG. 13A, the lowest temperature rise is produced when the 120,000 histotripsy pulses are equally distributed over the 10 minute total treatment time window (Scheme 1301).

When the therapy PRF is doubled and cooling steps are imposed (Schemes 1302-1304), the extent of the temperature rise is dependent on the distribution of cooling steps. A single long cooling step (Scheme 1302) results in the greatest temperature rise observed with this strategy. Conversely, shorter/more frequent cooling steps (Scheme 1304) more closely approximate the case of equally distributed pulses and result in the lowest temperature rise observed with this strategy.

Finally, Schemes 1305 and 1306 indicate that, for a set number of histotripsy pulses delivered within a given total treatment time window, a higher therapy:cooling time ratio (e.g., 3:1) is advantageous to a lower therapy:cooling time ratio (e.g., 1:3). Essentially, for a set number of histotripsy pulses delivered within a given time window, a lower PRF is thermally beneficial. This is consistent with the result of Scheme 1301, which indicates that the lowest possible PRF (achieved by uniformly distributing the histotripsy pulses within the given time window) produces the lowest temperature rise.

When Histotripsy is used to ablate a target volume larger than the cavitation bubble clouds created by the system, the cavitation focus of the Histotripsy therapy system is moved (mechanically or electronically) within the target volume to ablate the entire target volume. This disclosure provides methods and techniques that can improve the thermal profile of Histotripsy therapy when ablating a target tissue volume larger than the cavitation bubble cloud.

TABLE 1

| Sequence Strategy | Therapy Pulse PRF (Hz) | Bubble Manipulation (BM) Pulse PRF (Hz) | # Therapy Pulses: # BM Pulses (Ratio) | Total Treatment Time (min) |
|---|---|---|---|---|
| 1401 | 300 | 2400 | 1:7 | 24 |
| 1402 | 240 | 2400 | 1:9 | 30 |
| 1403 | 150 | 600 | 1:3 | 2 × 24 |
| 1404 | 150 | 600 | 1:3 | 48 |
| 1405 | 162 | 648 | 1:3 | 45 |

Table 1 describes a series of pulse sequence strategies including the PRF of the therapy pulse and the PRF of the bubble manipulation pulses, in addition to the total treatment time. Additionally, while sequences 1401, 1402, 1304, and 1405 ablate the entire target volume in a single "pass" of the bubble cloud across the target volume, sequence 1403 ablates the target volume with two "passes" of the bubble cloud. Comparing sequence 1404 to 1405, both sequences have a therapy PRF of 150 Hz, a bubble manipulation PRF of 600 Hz, and a total treatment time of 48 minutes, however sequence 1403 completes two "passes" of the bubble cloud across the target tissue volume, at 24 minutes per pass, compared to a single 48 minute "pass" in sequence 1404.

Figure 14A:
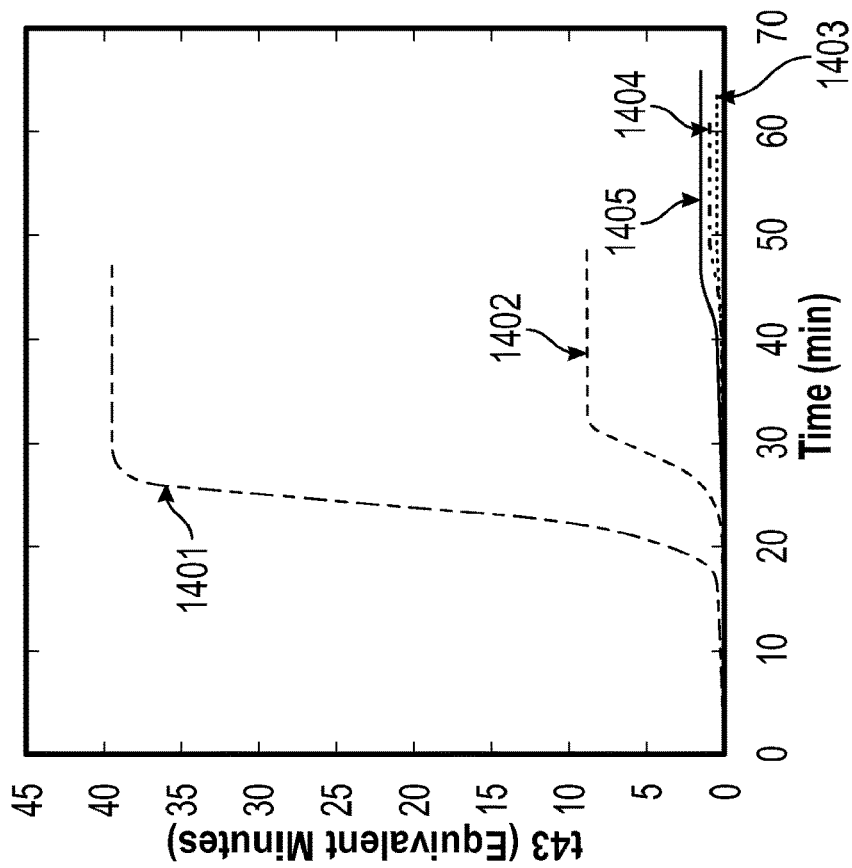
FIGS. 14A-14B illustrate temperature profiles resulting from three different histotripsy pulse schemes.
Figure 14B:
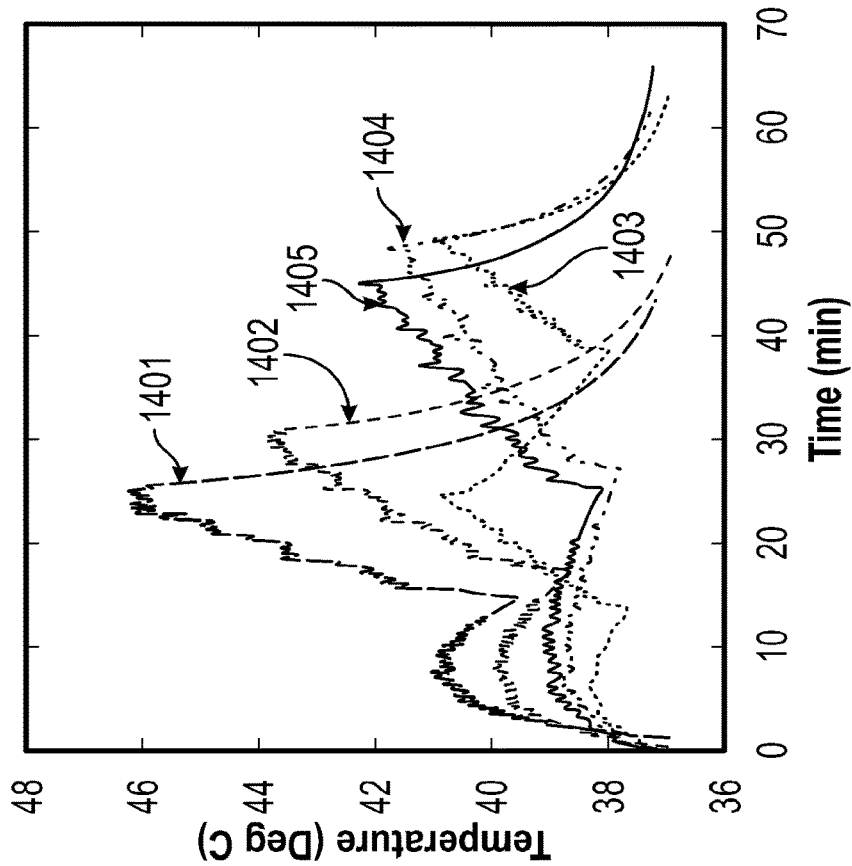

FIG. 14A illustrate the temperature profiles of the sequence strategies of Table 1, and FIG. 14B illustrate the resulting t43 curves produced during treatment. The lowest temperature rises are observed for the sequences that utilize the lowest therapy PRFs (1403 and 1404). Amongst these two, there is some thermal advantage to making multiple faster passes through the volume (sequence 1403 uses two 24 minute passes) in comparison to a single slower pass (sequence 1404 uses one 48 minute pass). The former strategy is likely to provide benefit by virtue of the fact that it allows for effective distribution of the incident acoustic energy in time and space. Rather than dwelling in any given location for an extended time, the enhanced motion of the transducer allows for one region of the volume to cool as another is being heated.

Sequences 1401 and 1402 have been observed to produce prefocal body wall injury during in-vivo liver treatment. Unsurprisingly, these sequences generate the greatest temperature rises of those illustrated.

The type of volume treatment path employed by the histotripsy systems described herein can also have implications on the thermal effect in tissue. As described above, some of the potential treatment patterns include the "Standard Z" (SZ) pattern, the "Top-Down" pattern, the "Bottom-Up" pattern, the "Standard Z Side-Side" pattern, the "Standard Z Shuffle" pattern, and the "Spiral In-Out" pattern.

TABLE 2

| Treatment | Pattern | Therapy On-Time | Cooling Time | Cooling Step Implementation | Total Time | % On-Time |
|---|---|---|---|---|---|---|
| No Cooling | SZ | 25:50 | 00:00 | N/A | 25:50 | 100% |
| Cooling Scheme 1 | SZ | 25:50 | 24:00 | Following Groups of Points | 49:50 | 51.8% |
| Cooling Scheme 2 | SZ | 25:50 | 24:00 | Point-by-Point | 49:50 | 51.8% |
| Cooling Scheme 3 | SZ | 25:50 | 12:55 | Point-by-Point | 38:45 | 66.7% |
| Cooling Scheme 4 | SZ | 25:50 | 51:40 | Point-by-Point | 1:17:30 | 33.3% |

Table 2 illustrates various cooling techniques performed with the SZ pattern. The SZ pattern without the incorporation of cooling steps served as the control. Cooling Schemes 1 and 2 both incorporated 24 minutes of total cooling. In Scheme 1 this cooling time was divided into 24 1-minute cooling steps, equally distributed throughout the treatment after a fixed number of treatment points. Conversely, in Scheme 2 the 24 minutes of cooling time was equally distributed after each treatment point. In these cases the incorporation of 24 minutes of cooling resulted in a percent on-time of 51.8%. Schemes 3 and 4 explore the influence of the therapy on-time:cooling-time ratio, with percent on-times of 66.7% and 33.3%, respectively. In both of these cases the cooling steps are equally distributed following each treatment point.

One of the advantageous features of the "DZ" treatment pattern is the fact that it provides logical points at which to implement cooling steps, such as a cooling time period. The alternating column (and analogously, alternating slices) approach allows for cooling steps during the motion time between the columns (and slices). In effect, the pattern has inefficiencies purposely built-in in order to accommodate strategically placed cooling times.

tation of the DZ pattern. Rather, this scheme is included solely to compare the thermal properties of the path to those of the SZ path.

The thermal profiles resulting from the five treatment schemes used to investigate the implementation of cooling steps during volume treatment are displayed in FIGS. 15A-15B. No cooling is shown in plot 1501, and cooling schemes 1-4 from Table 2 are illustrated as plots 1502-1505, respectively. As expected, the treatment conducted without the implementation of cooling (i.e., 100% on-time) produced the highest temperature rise ($\Delta t=12.7°$ C.). When cooling was implemented following each treatment point a reduction in temperature rise was observed, with volume treatments having percent on-times of 66.7% (Cooling Scheme 1504), 51.8% (Cooling Scheme 1503), and 33.3% (Cooling Scheme 1505) producing temperature rises of 10.5, 8.3, and 6.2° C., respectively.

Although an increased rate of pulse delivery is typically associated with increased thermal deposition, the decreased cavitation threshold associated with high PRF may act to offset this in such a way as to lead to lower overall temperature rises. Thus, the present disclosure also provides pulse sequences with relatively high PRFs that can be used to reduce thermal deposition in tissue.

TABLE 3

| Treatment Scheme | Pattern | Therapy On-Time (min) | Cooling Time (min) | Total Time (min) | % On-Time | Electronic Steering (cm) | Power Supply Setting |
|---|---|---|---|---|---|---|---|
| 1 | SZ | 31 | 0 | 31 | 100% | 0 | 50% |
| 2 | DZ, Bottom-Up | 31 | 0 | 31 | 100% | 0 | 50% |
| 3 | DZ, Bottom-Up | 31 | 13.5 | 44.5 | 70% | 0 | 50% |
| 4 | DZ, Bottom-Up | 31 | 45.5 | 76.5 | 41% | 0 | 50% |
| 5 | SZ | 31 | 0 | 31 | 100% | −1 | 50% |
| 6 | SZ | 31 | 0 | 31 | 100% | −2 | 61% |

Treatment schemes 3 and 4 in Table 3 above describe two varieties of implementing cooling steps into the DZ pattern. In Scheme 3 therapy is halted only during the motor motion between columns, which is anticipated to be the minimum cooling time implemented in the DZ sequence. In Scheme 4 additional cooling time is imposed beyond the time required for motor motion; this scheme was selected such as to give preliminary insight regarding the relationship between the temperature profile and the percent on-time of the volume treatment. It should be noted that Scheme 2, in which therapy was delivered over the entire motion path (including motions between columns), is not the intended implemen-

TABLE 4

| Treatment Scheme | Sequence | Pattern | Dose (Pulses/Point) | Total Time (min) | % On-Time | Power Supply Setting |
|---|---|---|---|---|---|---|
| 1 | 1601 | SZ | 943 (Average) | 25:50 | 100% | 50% |
| 2 | 1602 | DZ, Top-Down | 947 | 43:30 | 60% | 50% |

TABLE 4-continued

| Treatment Scheme | Sequence | Pattern | Dose (Pulses/Point) | Total Time (min) | % On-Time | Power Supply Setting |
|---|---|---|---|---|---|---|
| 3 | 1603 | DZC, Top-Down | 947 | 32:00 | 41% | 42% |

Figures 16A, 16B:
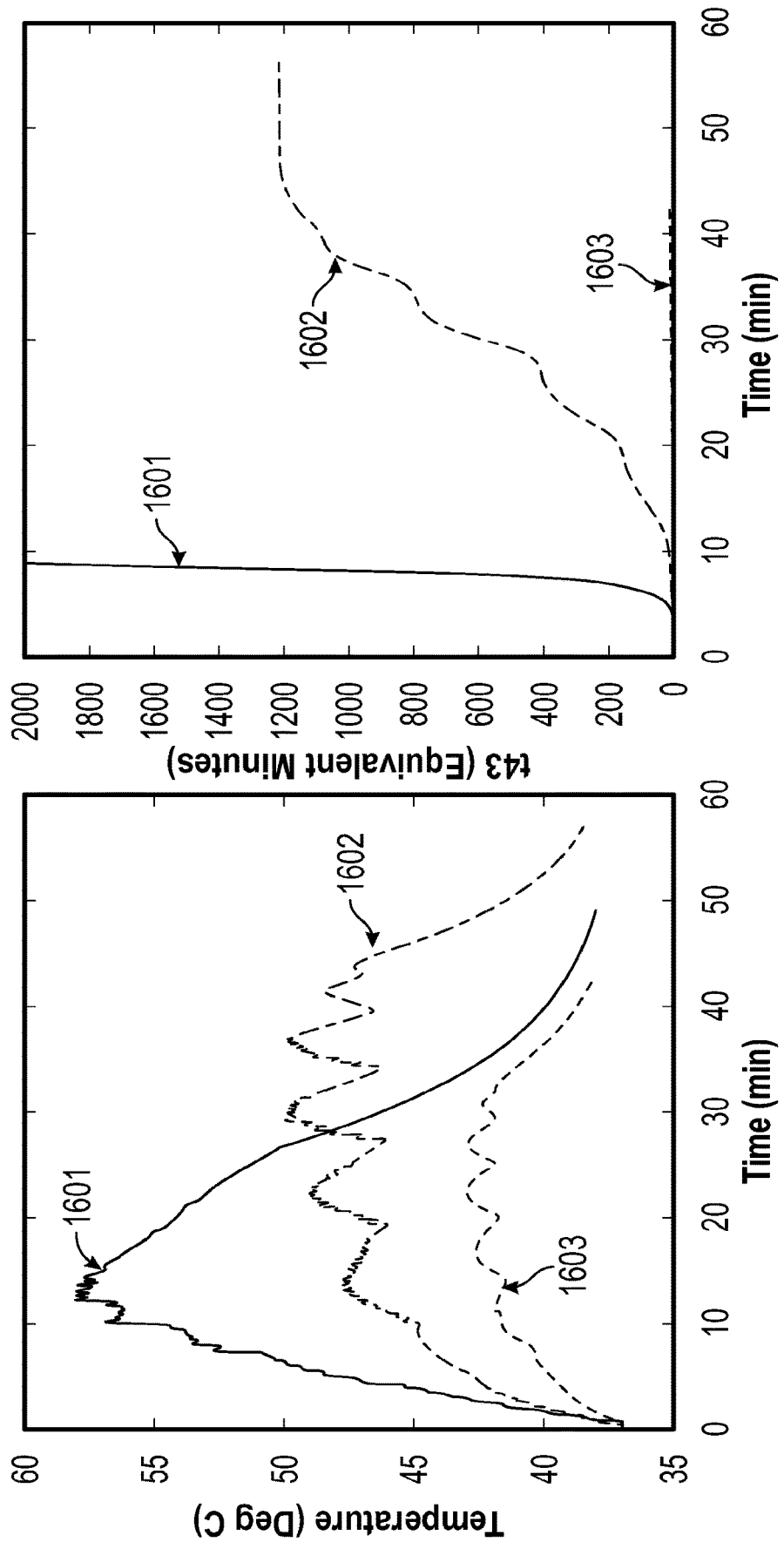
FIGS. 16A-16B illustrate the thermal effect of high-PRF sequences with cooling times.

FIGS. 16A-16B illustrate the thermal effect of high-PRF sequences with cooling times. Using the 1601 sequence with the SZ pattern produced a temperature rise of 21.2° C., whereas 1602 sequence with the top-down variant of the DZ pattern generated a temperature rise of 12.9° C. The corresponding t43 traces peaked at 1.43×10 5 and 1.21×10 3 equivalent minutes, respectively.

The implementation of sequence 1603 in the top-down variant of the DZC pattern produced further reduction in thermal deposition, with a temperature rise of only 6.2° C. and peak t43 of 9.6 equivalent minutes. As such, it appears that the high-PRF strategy is extremely promising for reducing prefocal thermal effects. On first pass increasing the pulse rate as a means of reducing thermal deposition may seem counterintuitive, as temperature rise scales linearly with the rate of pulse application at a given amplitude. However, the decreased bubble cloud initiation threshold associated with higher PRFs appears to significantly outweigh this effect. This is the result of the fact that temperature increase scales with the square of the pulse amplitude; as such, if the threshold amplitude discrepancy is great enough, the thermal benefit of lower pressure will dominate over the thermal drawback of increased pulse rate.

In addition to the apparent thermal benefits, there is a second major advantage of increased therapy PRF: a reduction in treatment time. This is illustrated by Schemes 2 and 3, which both used (essentially) the same pattern with the same amount of cooling time (cooling only during inter-column motions). In this case delivering a dose of 947 pulses/point required a total treatment time of 43:30 with sequence 1602; delivering the same dose with sequence 1603 required only 32:00.

Treatment Planning

Figure 17A:
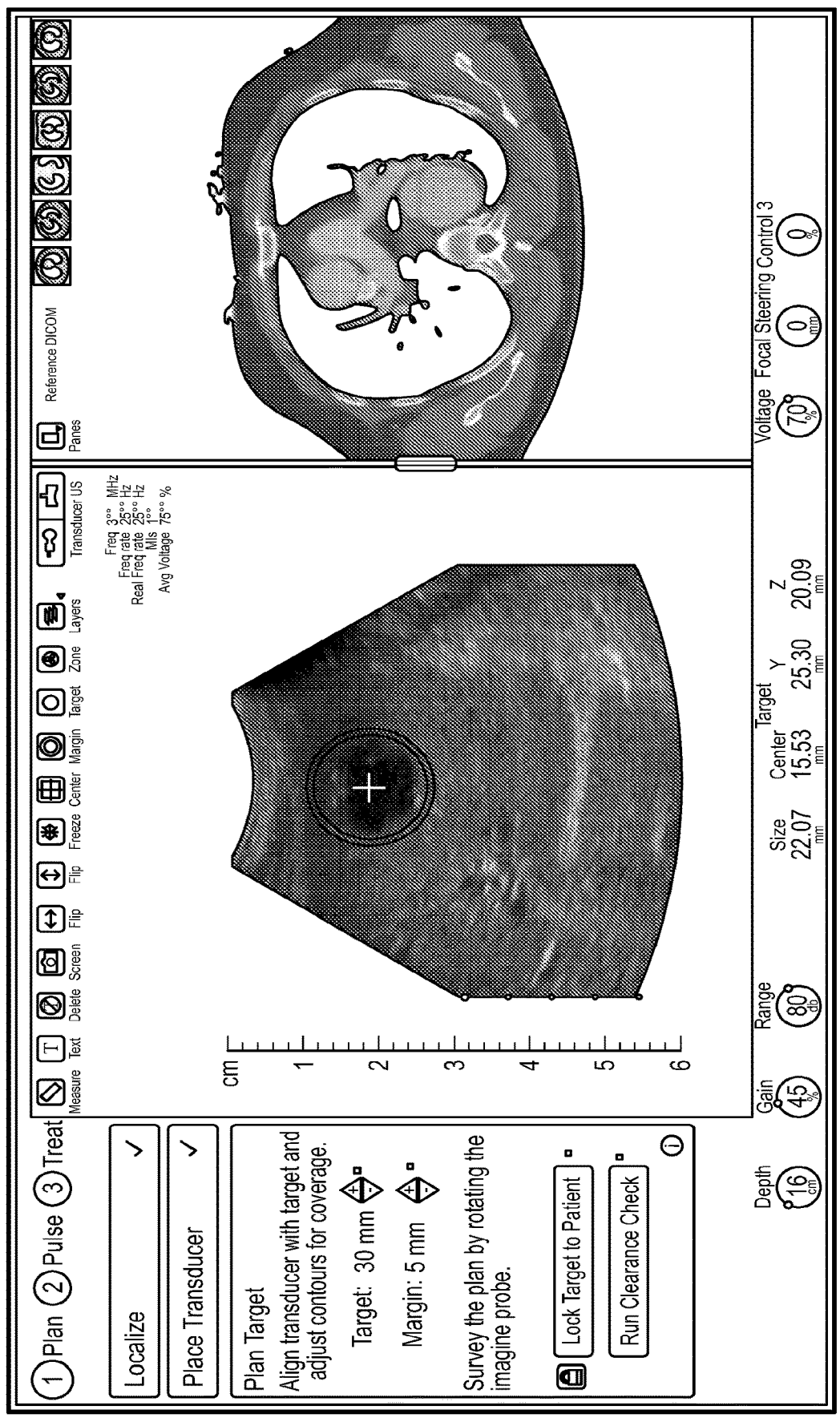
FIGS. 17A-17E illustrate examples of a graphical user interface of the system.
Figure 17B:
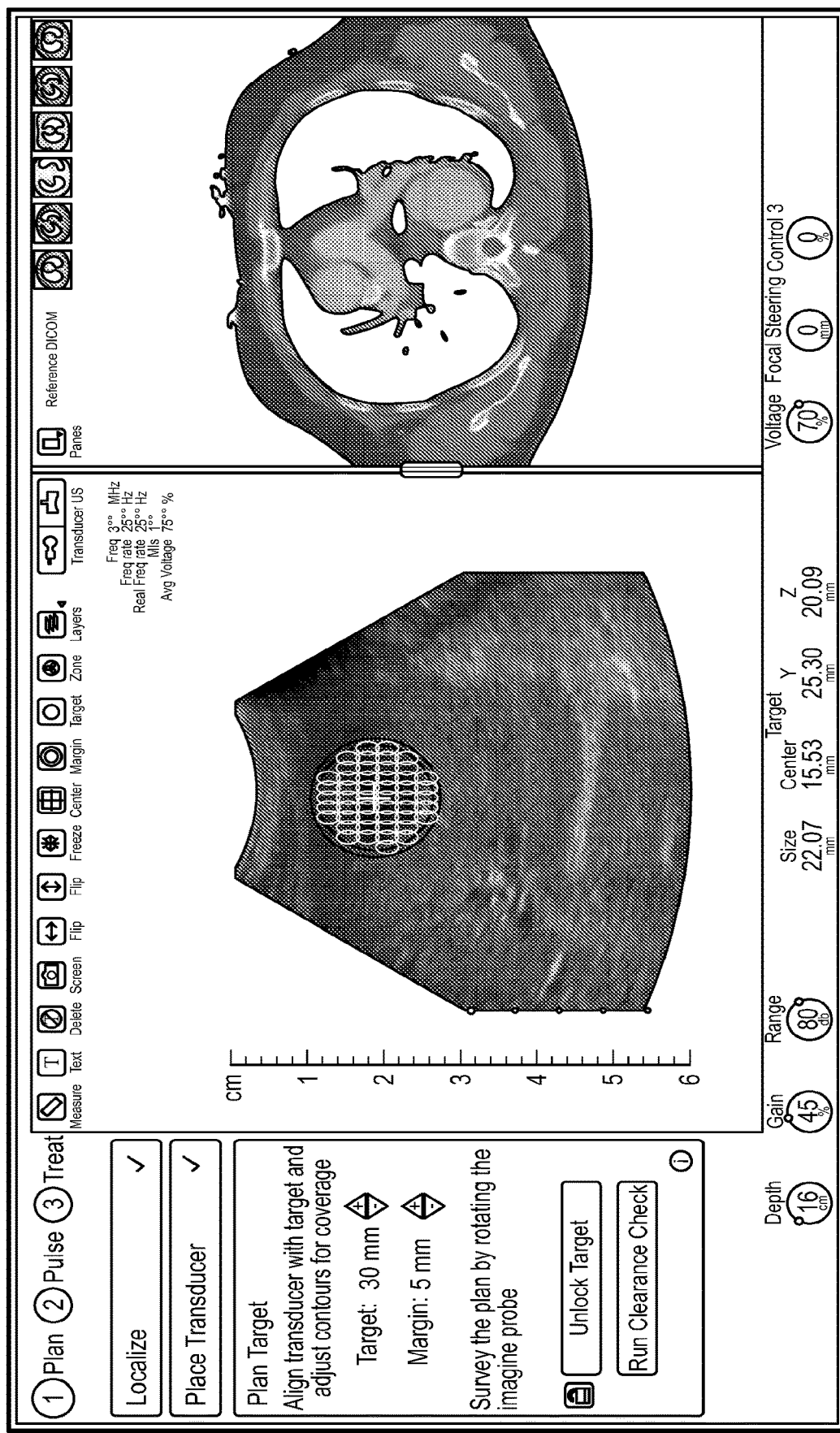

Systems and methods are further described herein that include a graphical user interface (GUI) used to plan and carry out ablation therapies. Referring to FIGS. 17A-17E, a GUI of the present disclosure can include one or more internal views of a patient, including a target tissue volume. An operator (such as a physician) can identify the target tissue volume in the real-time imaging and mark both the target tissue volume and a desired margin around the target tissue volume in the system. The system can automatically calculate/determine the size of the target tissue volume from the selection, as well as calculate planned treatment time for a specific set of treatment parameters for user defined targets and regions of interest. Referring to FIG. 17B, the GUI can overlay on top of the target tissue volume a chosen treatment plan and pattern, including configurable views of treatment and bubble cloud locations and spacing, which can be preselected, or user selected, from any of the treatment patterns described above (e.g., SZ pattern, DZ pattern, etc.).

Figure 17C:
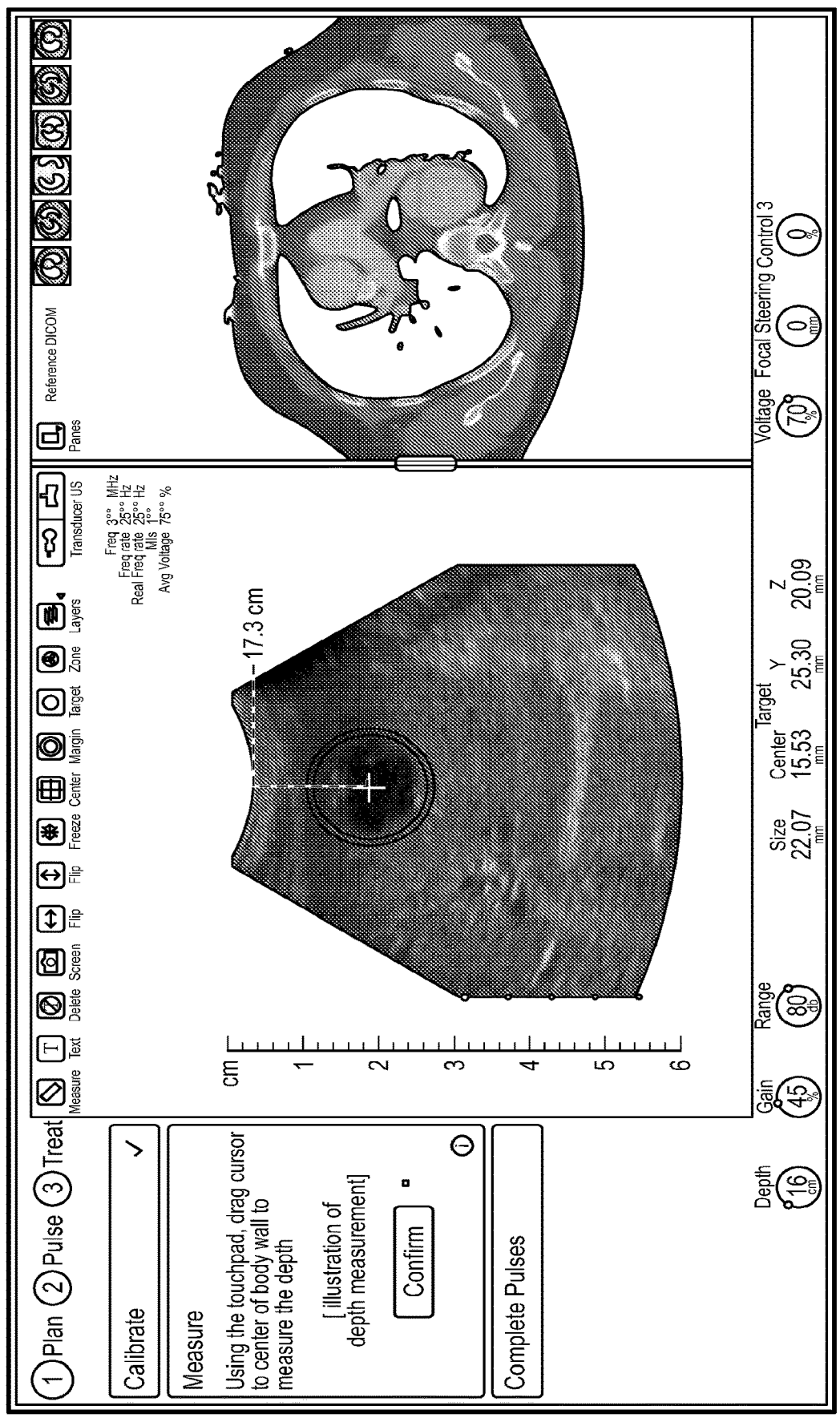

In some embodiments, the depth of the target tissue volume can be a factor in determining which pulse sequence parameters and/or treatment patterns to use, and/or part of the treatment algorithm, including as part, and an input to an embedded treatability matrix or look up table. Thus, the GUI can further enable the user to measure the depth of the target treatment volume, as shown in FIG. 17C.

Figure 17D:
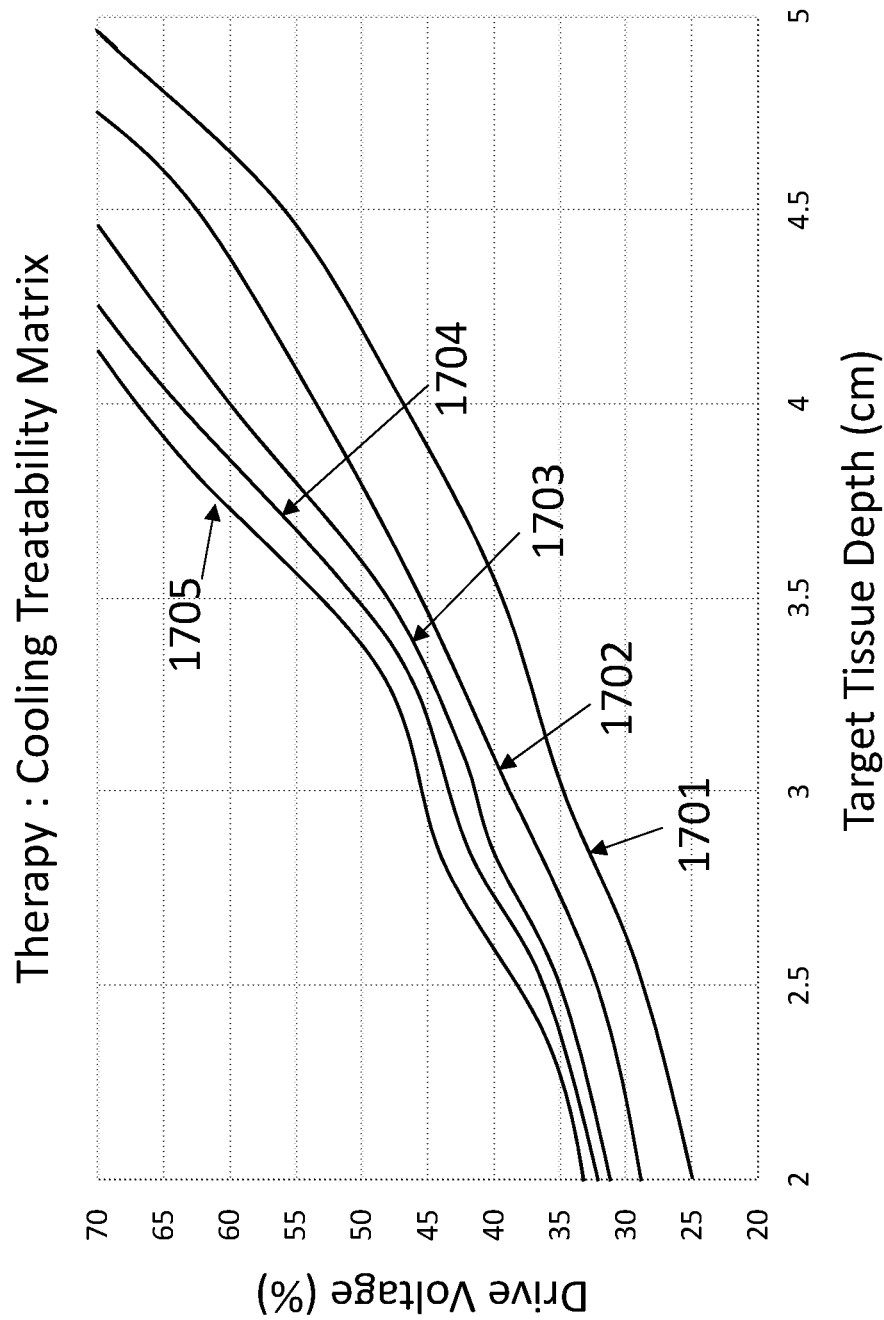

FIG. 17D illustrates one example of a Therapy:Cooling Treatability Matrix or look-up table, which can be used during therapy to determine the appropriate treatment and cooling parameters to prevent or reduce thermal injury to non-targeted tissue sites. In some examples, the histotripsy system can automatically use the depth of the target tissue and the selected drive voltage % to determine optimal pulse parameters, including the ratio of treatment pulses to cooling time, that will avoid tissue damage to non-targeted tissues. This implementation therefore advantageously eliminates or reduces the risk of, for example, damage or heating to pre-focal tissues located between the target tissue and the therapy transducer.

The Therapy:Cooling Treatability Matrix uses the selected drive voltage (%) and the target tissue depth (in cm) to automatically determine the ratio of therapy to cooling time during a given treatment session. As described above, a 1:1 ratio of therapy to cooling will have equal amounts of time during a treatment session dedicated to therapy pulse delivery and to cooling periods (periods in which no therapy is delivered). For example, if the therapy total treatment time is 30 minutes and the therapy:cooling ratio is 1:1, then 15 minutes of the total treatment time will be spent delivering therapy pulses to tissue, and 15 minutes of the total treatment time will be spent delivering no therapy pulses to tissue (e.g., repositioning the therapy transducer for delivery of subsequent bubble clouds).

Referring back to the treatability matrix of FIG. 17D, the drive voltage and target tissue depth are used to determine the ratio of therapy to cooling to avoid non-targeted tissue damage. For drive voltage and target tissue depth combinations falling in the region between line 1701 and the x-axis of FIG. 17D, a first cooling ratio can be applied to the therapy pulse sequence to avoid unwanted tissue damage. In one example, the first cooling ratio can comprise a 1:1 ratio of therapy to cooling (e.g., for a given treatment time, therapy is delivered 50% of the treatment time and cooling, or no therapy, is applied 50% of the treatment time). For drive voltage and target tissue depth combinations falling in the region between line 1701 and line 1702, a second cooling ratio can be applied to the therapy pulse sequence to avoid unwanted tissue damage. In one example, the second cooling ratio can comprise a 1:2 ratio of therapy to cooling (e.g., for a given treatment time, therapy is delivered 33% of the treatment time and cooling, or no therapy, is applied 67% of the treatment time). For drive voltage and target tissue depth combinations falling in the region between line 1702 and line 1703, a third cooling ratio can be applied to the therapy pulse sequence to avoid unwanted tissue damage. In one example, the third cooling ratio can comprise a 1:3 ratio of therapy to cooling (e.g., for a given treatment time, therapy is delivered 25% of the treatment time and cooling, or no therapy, is applied 75% of the treatment time). For drive voltage and target tissue depth combinations falling in the region between line 1703 and line 1704, a fourth cooling ratio can be applied to the therapy pulse sequence to avoid unwanted tissue damage. In one example, the fourth cooling ratio can comprise a 1:4 ratio of therapy to cooling (e.g., for a given treatment time, therapy is delivered 20% of the treatment time and cooling, or no therapy, is applied 80% of the treatment time). For drive voltage and target tissue depth combinations falling in the region between line 1704 and line 1705, a fifth cooling ratio can be applied to the therapy pulse sequence to avoid unwanted tissue damage. In one example, the fifth cooling ratio can comprise a 1:5 ratio of therapy to cooling (e.g., for a given treatment time, therapy is delivered 16% of the treatment time and cooling, or no therapy, is applied 84% of the treatment time). It should be understood that the exact cooling ratios described herein as examples can be adjusted depending on the target tissue type, total treatment time, transducer type, driving amplifier, target tissue size, depth, etc.

Figure 17E:
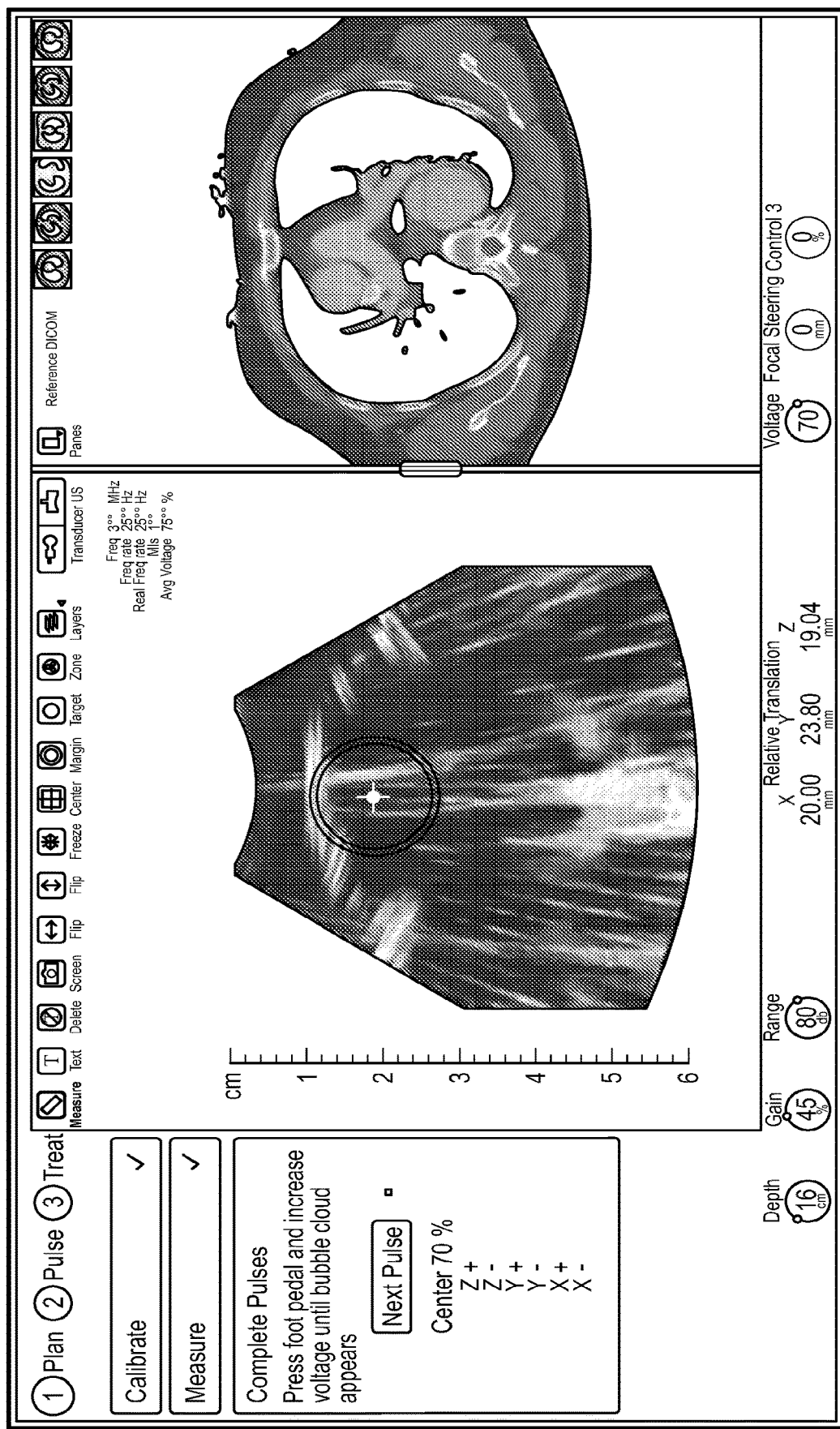

Referring to FIG. 17E, the real-time imaging can be used to guide the user during the therapy itself. For example, in one embodiment, the user can be instructed to increase the driving voltage of the therapy transducer(s) until a bubble cloud appears in the real-time imaging. The bubble cloud or cavitation will appear in the tissue when the driving voltage achieves the cavitation threshold required of the selected target tissue location. This may further include guiding a user through a test pulse protocol to inform a patient/target specific treatment plan that accounts for the combination of, but not limited to, sequence, pattern, pathway and any intervening tissue/blockage, to ensure robust tissue effect and minimal and/or no collateral damage to adjacent or intervening tissue.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), and/or any structure capable of providing temporary procedure support (e.g., tent). In some cases, systems and/or sub-systems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design.

What is claimed is:

1. An ultrasound therapy system, comprising;
a robotic positioning system;
an ultrasound therapy transducer array connected to the robotic positioning system;
a generator operatively coupled to the ultrasound therapy transducer array, the generator and ultrasound therapy transducer array being configured to deliver histotripsy pulses into a subject to generate cavitation in the subject;
at least one processor operatively coupled to the robotic positioning system and the generator, the at least one processor being configured to control the robotic positioning system and the generator to provide histotripsy therapy to the subject according to a treatment plan that includes a plurality of treatment volumes within a target tissue volume of the subject by:
controlling the robotic positioning system to mechanically position a focus of the ultrasound therapy transducer array within a first of the plurality of treatment volumes;
controlling the generator to deliver histotripsy pulses with the ultrasound therapy transducer array to form a cavitation bubble cloud at the focus;
controlling the generator to electronically steer the cavitation bubble cloud through the first of the plurality of treatment volumes; and
repeating controlling the robotic positioning system and the generator to mechanically position the focus, controlling the generator to form the cavitation bubble cloud at the focus, and controlling the generator to electronically steer the focus for each of the plurality of treatment volumes.

2. The ultrasound therapy system of claim 1, wherein the generator comprises a field programmable gate array.

3. The ultrasound therapy system of claim 1, further comprising an imaging system configured to image the cavitation bubble cloud in real-time.

4. The ultrasound therapy system of claim 3, further comprising a display configured to display the cavitation bubble cloud in real-time.

5. The ultrasound therapy system of claim 1, wherein the ultrasound therapy system is configured to communicate with an imaging system selected from the group consisting of Magnetic Resonance Imaging (MRI), Computed Tomography (CT), cone beam CT (CBCT), Positron Emission Tomography-Computed Tomography (PET-CT), and/or an ultrasound imaging system.

6. The ultrasound therapy system of claim 3, wherein the imaging system comprises an ultrasound imaging probe configured within a bore of the ultrasound therapy transducer array.

7. The ultrasound therapy system of claim 1, wherein the one or more processors receive the treatment plan.

8. The ultrasound therapy system of claim 1, wherein the one or more processors are configured to generate the treatment plan.

9. The ultrasound therapy system of claim 1, wherein the target tissue volume of the treatment plan has a shape selected from the group consisting of generally spherical, an ellipsoid, and an arbitrary shape.

10. The ultrasound therapy system of claim 1, wherein the target tissue volume of the treatment plan is contoured to a tumor of the subject.

11. The ultrasound therapy system of claim 1, wherein the target tissue volume of the treatment plan includes a margin.

12. The ultrasound therapy system of claim 1, wherein the at least one processor is configured to mechanically move the focus through the plurality of treatment volumes in a generally spiraling fashion through the target tissue volume.

13. The ultrasound therapy system of claim 1, wherein the at least one processor is configured to mechanically move the focus through the plurality of treatment volumes from distal to proximal through the target tissue volume.

14. The ultrasound therapy system of claim 1, wherein the plurality of treatment volumes are column-shaped.

15. The ultrasound therapy system of claim 1, wherein the plurality of treatment volumes are arranged in radial layers.

16. An ultrasound therapy system, comprising;
a robotic positioning system;
an ultrasound therapy transducer array connected to the robotic positioning system;
a generator operatively coupled to the ultrasound therapy transducer array, the generator and ultrasound therapy transducer array being configured to deliver histotripsy pulses into a subject to generate cavitation in the subject;
at least one processor operatively coupled to the robotic positioning system and the generator, the at least one processor being configured to control the robotic positioning system and the generator to provide histotripsy therapy to the subject according to a treatment plan that includes a plurality of treatment volumes within a target tissue volume of the subject by:

controlling the robotic positioning system to mechanically position a focus of the ultrasound therapy transducer array within a first of the plurality of treatment volumes;

controlling the generator to deliver histotripsy pulses with the ultrasound therapy transducer array to form a first cavitation bubble cloud at the focus;

controlling the generator to electronically steer the first cavitation bubble cloud through the first of the plurality of treatment volumes; and controlling the robotic positioning system to mechanically position the focus of the ultrasound therapy transducer array within a second of the plurality of treatment volumes;

controlling the generator to deliver histotripsy pulses with the ultrasound therapy transducer array to form a second cavitation bubble cloud at the focus;

controlling the generator to electronically steer the second cavitation bubble cloud through the second of the plurality of treatment volumes.

17. The ultrasound therapy system of claim 16, wherein the at least one processor is configured to repeat controlling the robotic positioning system and the generator to mechanically position the focus, controlling the generator to form subsequent cavitation bubble clouds at the focus, and controlling the generator to electronically steer the focus for each of a remaining plurality of treatment volumes.

18. The ultrasound therapy system of claim 16, wherein the ultrasound therapy system is configured to communicate with an imaging system selected from the group consisting of Magnetic Resonance Imaging (MRI), Computed Tomography (CT), cone beam CT (CBCT), Positron Emission Tomography-Computed Tomography (PET-CT), and an ultrasound imaging system.

19. The ultrasound therapy system of claim 18, wherein the imaging system is configured to image the cavitation bubble cloud in real-time.

20. The ultrasound therapy system of claim 19, further comprising a display configured to display the cavitation bubble cloud in real-time.

\* \* \* \* \*